United States Patent
Schoenfisch et al.

(10) Patent No.: US 10,435,357 B2
(45) Date of Patent: Oct. 8, 2019

(54) TUNABLE NITRIC OXIDE-RELEASING MACROMOLECULES HAVING MULTIPLE NITRIC OXIDE DONOR STRUCTURES

(71) Applicants: The University of North Carolina at Chapel Hill, Chapel Hill, NC (US); Novan, Inc., Morrisville, NC (US)

(72) Inventors: Mark Schoenfisch, Chapel Hill, NC (US); Yuan Lu, Chapel Hill, NC (US); Nathan Stasko, Chapel Hill, NC (US); Jian Bao, Cary, NC (US)

(73) Assignees: The University of North Carolina at Chapel Hill, Chapel Hill, NC (US); Novan, Inc., Morrisville, NC (US)

( * ) Notice: Subject to any disclaimer, the term of this patent is extended or adjusted under 35 U.S.C. 154(b) by 0 days.

(21) Appl. No.: 16/239,069

(22) Filed: Jan. 3, 2019

(65) Prior Publication Data

US 2019/0135738 A1    May 9, 2019

Related U.S. Application Data

(63) Continuation of application No. 14/961,133, filed on Dec. 7, 2015, now Pat. No. 10,196,349, which is a continuation of application No. 14/184,156, filed on Feb. 19, 2014, now Pat. No. 9,238,038, which is a continuation of application No. PCT/US2012/052350, filed on Aug. 24, 2012.

(60) Provisional application No. 61/526,918, filed on Aug. 24, 2011.

(51) Int. Cl.
| | |
|---|---|
| *C07C 281/20* | (2006.01) |
| *A61K 31/655* | (2006.01) |
| *A61K 9/14* | (2006.01) |
| *C07C 291/02* | (2006.01) |
| *C07C 247/10* | (2006.01) |

(52) U.S. Cl.
CPC .......... *C07C 281/20* (2013.01); *A61K 31/655* (2013.01); *C07C 247/10* (2013.01); *C07C 291/02* (2013.01); *Y10T 428/2982* (2015.01)

(58) Field of Classification Search
CPC ..... A61K 31/655; A61K 9/145; C07C 247/10
See application file for complete search history.

(56) References Cited

U.S. PATENT DOCUMENTS

| | | | |
|---|---|---|---|
| 8,591,876 B2 | 11/2013 | Bauman et al. | |
| 2009/0068248 A1 | 3/2009 | Waterhouse et al. | |
| 2009/0214618 A1 | 8/2009 | Schoenfisch et al. | |
| 2010/0098733 A1 | 4/2010 | Stasko | |
| 2012/0134951 A1 | 5/2012 | Stasko et al. | |
| 2012/0136323 A1 | 5/2012 | Stasko et al. | |
| 2014/0271523 A1 | 9/2014 | Milbocker et al. | |

FOREIGN PATENT DOCUMENTS

WO    2013006608    1/2013

OTHER PUBLICATIONS

Extended European Search Report corresponding to European Patent Application No. 12825927.2 (5 pages) (dated Mar. 5, 2015).
International Preliminary Report on Patentability corresponding to International Patent Application No. PCT/US2012/052350 (7 pages) (dated Feb. 25, 2014).
International Search Report and the Written Opinion of the International Searching Authority corresponding to International Patent Application No. PCT/US2012/052350 (13 pages) (dated Nov. 13, 2012).
Kayastha et al. "An Easy Method to Determine the Kinetic Parameters of Biphasic Reactions" Biochemical Education, 15(3):135 (1987).
Lu et al. "Structurally Diverse Nitric Oxide-Releasing Poly(propylene imine) Dendrimers" Chemistry of Materials 23:4227-4233 (2011).
Marxer et al. "Preparation of Nitric Oxide (NO)-Releasing Sol-Gels for Biomaterial Applications" Chemistry of Materials, 15:4193-4199 (2003).
Riccio et al. "Nitric Oxide Release Part I. Macromolecular Scaffolds" Chemical Society Reviews 41(10):3731-3741 (2012).
Schaffer et al. "Diabetes-impaired healing and reduced wound nitric oxide synthesis: A possible pathophysiologic correlation" Surgery 121(5):513-519 (1997).
Shi et al. "The role of iNOS in wound healing" Surgery 130(2):225-229 (2001).
Shin et al. "Synthesis of Nitric Oxide-Releasing Silica Nanoparticles" Journal of the American Chemical Society 127:4612-4619 (2007).
Shin et al. "Inorganic/Organic Hybrid Silica Nanoparticles as a Nitric Oxide Delivery Scaffold" Chemistry of Materials, 20:239-249 (2008).
Stasko et al. "S-Nitrosothiol-Modified Dendrimers as Nitric Oxide Delivery Vehicles" Biomacromolecules 9:834-841 (2008).

*Primary Examiner* — Robert H Havlin

(74) *Attorney, Agent, or Firm* — Myers Bigel, P.A.

(57) ABSTRACT

Provided here are nitric oxide-releasing compounds that include at least two different NO donor functional groups of the same class. In some embodiments, such nitric oxide-releasing compounds are macromolecules such as dendrimer and co-condensed silica. Pharmaceutical compositions, wound dressings, kits and methods of treatments are also provided herein.

20 Claims, 14 Drawing Sheets

TUNABLE NITRIC OXIDE-RELEASING MACROMOLECULES HAVING MULTIPLE NITRIC OXIDE DONOR STRUCTURES

RELATED APPLICATION DATA

This application is a continuation of U.S. patent application Ser. No. 14/961,133, filed on Dec. 7, 2015, which is a continuation of U.S. patent application Ser. No. 14/184,156, filed on Feb. 19, 2014, which is a continuation under 35 U.S.C. § 111(a) of PCT Application No. PCT/US2012/052350, filed on Aug. 24, 2012, which claims the benefit, under 35 U.S.C. § 119, of U.S. Provisional Application Ser. No. 61/526,918, filed Aug. 24, 2011, the disclosure of each of which is hereby incorporated by reference herein in its entirety.

STATEMENT OF GOVERNMENT SUPPORT

This invention was made with government support under Grant No. EB000708 awarded by the National Institutes of Health. The government has certain rights in the invention.

FIELD OF THE INVENTION

The present invention relates to compounds that release nitric oxide. More particularly, the present invention relates to macromolecular compositions for tuning nitric oxide-release kinetics for therapeutic purposes.

BACKGROUND OF THE INVENTION

It is known that nitric oxide possesses a broad-spectrum of antimicrobial activity and may be used as an alternative to conventional antibiotics for drug resistant bacteria. Furthermore, some recent studies have demonstrated that nitric oxide may also play an important role in the wound healing process by promoting angiogenesis through stimulation of vascular endothelial growth factor (VEGF) and increased fibroblast collagen synthesis. See Schaffer M R, et al., *Diabetes-impaired healing and reduced wound nitric oxide synthesis: A possible pathophysiologic correlation*. Surgery 1997; 121(5):513-9; and Shi H P, et al., *The role of iNOS in wound healing*. Surgery 2001; 130 (2):225-9. Thus, nitric oxide presents a promising addition and/or alternative to the conventional antibiotic treatment for wound care.

Nitric oxide is a gas at ambient temperature and atmospheric pressure, and it has a short half-life in a physiological milieu. Several small molecule nitric oxide donor pro-drugs have been developed which have contributed greatly to the understanding of nitric oxide in a number of disease states. However, due to issues with stability, indiscriminate NO-release, monotypical nitric oxide release kinetics, and inability to target specific tissue types, no clinically viable solutions currently exist for administering nitric oxide outside of its gaseous form. Reproducibly delivering the appropriate levels of nitric oxide for a given therapeutic indication is important because release of large amounts of nitric oxide may be toxic or create undesirable side effects such as decreases in angiogenesis or increased inflammation. Therefore, it has been challenging to use nitric oxide in a therapeutic setting, other than via exogenous application, particularly in topical applications wherein nitric oxide has concentration dependent effects and benefits from delivery in a controlled and targeted manner.

Dendrimers are a family of hyperbranched macromolecules with multivalent surfaces that enable the design of targeted therapeutics agent delivery vehicles. For example, polyamidoamines, polyamines, polypeptides, polyesters and polyethers dendrimers have been utilized for a range of biomedical applications, including drug and gene delivery, biological imaging, and tissue engineering. Dendimers have been also been used as macromolecular nitric oxide donors.

Inorganic-organic hybrid silica nanoparticles have also been explored for applications spanning separation, biological labelling, diagnostics, and carrier systems for the controlled delivery of drugs. The drug delivery potential of silica particles has received much attention because of their physical and chemical versatility and non-toxic nature. Other materials, including functionalized metallic nanoparticles, have also been used in drug delivery. Such nanoparticles have also been used as macromolecular nitric oxide donors.

SUMMARY OF THE INVENTION

Provided according to embodiments of the invention are nitric oxide-releasing macromolecules that include at least two different NO donor structures of the same class. Also provided are pharmaceutical compositions that include a nitric oxide-releasing macromolecule according to an embodiment of the invention, and methods of administering such macromolecules and/or compositions to a subject.

BRIEF DESCRIPTION OF THE FIGURES

The foregoing and other objects, features and advantages of the invention will become more apparent from the following more particular description of exemplary embodiments of the invention and the accompanying drawings. The drawings are not necessarily to scale, emphasis instead being placed upon illustrating the principles of the invention.

DETAILED DESCRIPTION OF SOME EMBODIMENTS OF THE INVENTION

Figure 1:
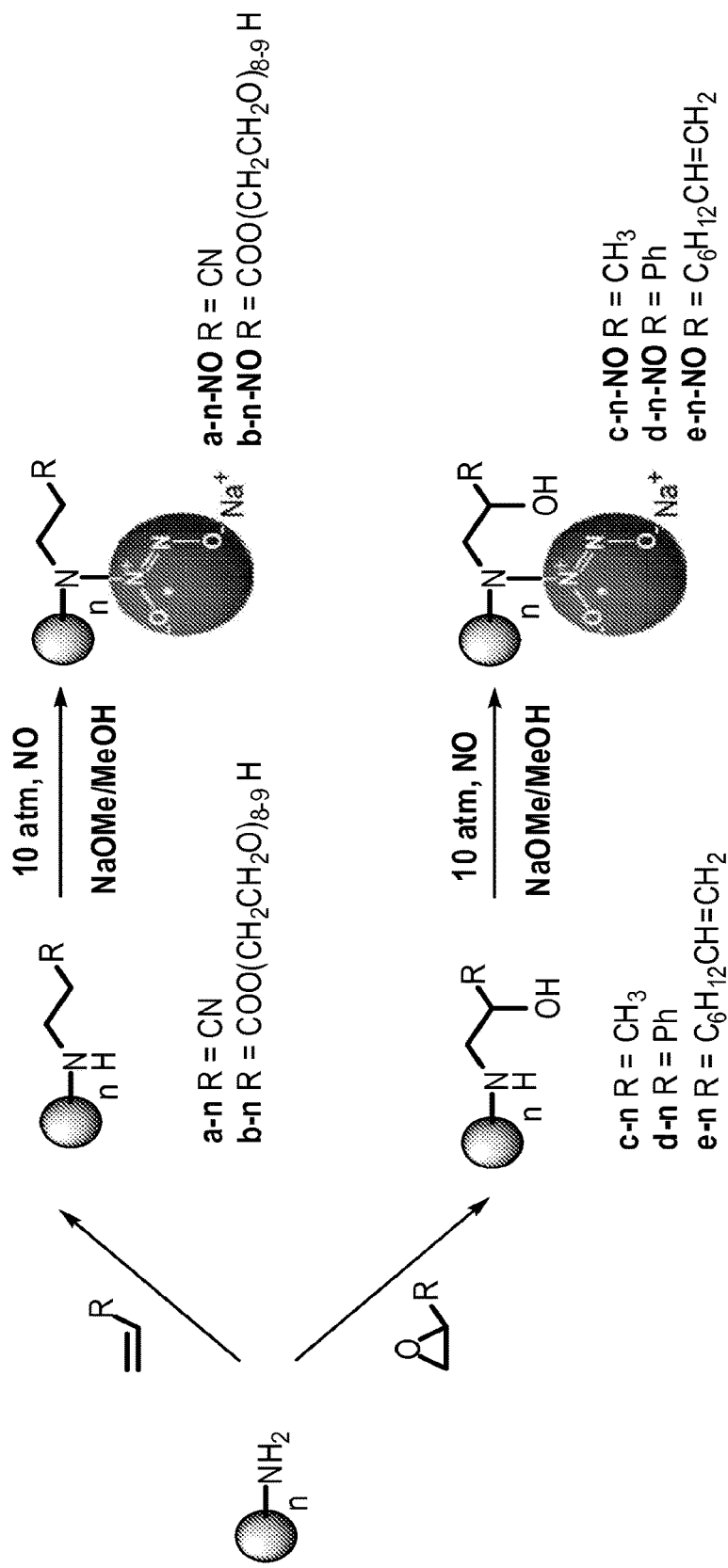
FIG. 1 is a schematic of the synthesis of secondary amine- and diazeniumdiolate-functionalized PPI conjugates, wherein n represents the number of primary amines on the periphery of PPI dendrimers (n=8, 16, 32, and 64).

The foregoing and other aspects of the present invention will now be described in more detail with respect to the description and methodologies provided herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the embodiments of the invention and the appended claims, the singular forms "a", "an" and "the" are intended to include the plural forms as well, unless the context clearly indicates otherwise. Also, as used herein, "and/or" refers to and encompasses any and all possible combinations of one or more of the associated listed items. Furthermore, the term "about," as used herein when referring to a measurable value such as an amount of a compound, dose, time, temperature, and the like, is meant to encompass variations of 20%, 10%, 5%, 1%, 0.5%, or even 0.1% of the specified amount. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Unless otherwise defined, all terms, including technical and scientific terms used in the description, have the same meaning as commonly understood by one of ordinary skill in the art to which this invention belongs. All patents, patent applications and publications referred to herein are incorporated by reference in their entirety. In the event of conflicting terminology, the present specification is controlling.

The embodiments described in one aspect of the present invention are not limited to the aspect described. The embodiments may also be applied to a different aspect of the invention as long as the embodiments do not prevent these aspects of the invention from operating for its intended purpose.

Chemical Definitions

As used herein the term "alkyl" refers to $C_{1-20}$ inclusive, linear (i.e., "straight-chain"), branched, or cyclic, saturated or at least partially and in some cases fully unsaturated (i.e., alkenyl and alkynyl) hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and alkenyl groups. "Branched" refers to an alkyl group in which a lower alkyl group, such as methyl, ethyl or propyl, is attached to a linear alkyl chain. Exemplary branched alkyl groups include, but are not limited to, isopropyl, isobutyl, tert-butyl. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-5}$ straight-chain alkyls. In other embodiments, "alkyl" refers, in particular, to $C_{1-5}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the Willi "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "aryl" is used herein to refer to an aromatic substituent that can be a single aromatic ring, or multiple aromatic rings that are fused together, linked covalently, or linked to a common group, such as, but not limited to, a methylene or ethylene functional group. The common linking group also can be a carbonyl, as in benzophenone, or oxygen, as in diphenylether, or nitrogen, as in diphenylamine. The term "aryl" specifically encompasses heterocyclic aromatic compounds. The aromatic ring(s) can comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings.

The aryl group can be optionally substituted (a "substituted aryl") with one or more aryl group substituents, which can be the same or different, wherein "aryl group substituent" includes alkyl, substituted alkyl, aryl, substituted aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NR$^1$R", wherein R$^1$ and R" can each be independently hydrogen, alkyl, substituted alkyl, aryl, substituted aryl, and aralkyl.

Thus, as used herein, the term "substituted aryl" includes aryl groups, as defined herein, in which one or more atoms or functional groups of the aryl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto. Specific examples of aryl groups include, but are not limited to, cyclopentadienyl, phenyl, furan, thiophene, pyrrole, pyran, pyridine, imidazole, benzimidazole, isothiazole, isoxazole, pyrazole, pyrazine, triazine, pyrimidine, quinoline, isoquinoline, indole, carbazole, and the like.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl.

"Alkoxyl" refers to an alkyl-O— group wherein alkyl is as previously described. The term "alkoxyl" as used herein can refer to, for example, methoxyl, ethoxyl, propoxyl, isopropoxyl, butoxyl, f-butoxyl, and pentoxyl. The term "oxyalkyl" can be used interchangeably with "alkoxyl". In some embodiments, the alkoxyl has 1, 2, 3, 4, or 5 carbons.

"Aralkyl" refers to an aryl-alkyl group wherein aryl and alkyl are as previously described, and include substituted aryl and substituted alkyl. Exemplary aralkyl groups include benzyl, phenylethyl, and naphthylmethyl.

"Alkylene" refers to a straight or branched bivalent aliphatic hydrocarbon group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—CH$_2$—); ethylene (—CH$_2$—CH$_2$—); propylene (—(CH$_2$)$_3$—); cyclohexylene (—C$_6$H$_{10}$—); —CH=CH—CH=CH—; —CH=CH—CH$_2$—; wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—CH$_2$—O—); and ethylenedioxyl (—O—(CH$_2$)$_2$—O—). An alkylene group can have about 2 to about 3 carbon atoms and can further have 6-20 carbons.

"Arylene" refers to a bivalent aryl group. An exemplary arylene is phenylene, which can have ring carbon atoms available for bonding in ortho, meta, or para positions with regard to each other, i.e., respectively. The arylene group can also be napthylene. The arylene group can be optionally substituted (a "substituted arylene") with one or more "aryl group substituents" as defined herein, which can be the same or different.

"Aralkylene" refers to a bivalent group that contains both alkyl and aryl groups. For example, aralkylene groups can have two alkyl groups and an aryl group (i.e., -alkyl-aryl-alkyl-), one alkyl group and one aryl group (i.e., -alkyl-aryl-) or two aryl groups and one alkyl group (i.e., -aryl-alkyl-aryl-).

The term "amino" and "amine" refer to nitrogen-containing groups such as NR$_3$, NH$_3$, NHR$_2$, and NH$_2$R, wherein R can be alkyl, branched alkyl, cycloalkyl, aryl, alkylene, arylene, aralkylene. Thus, "amino" as used herein can refer to a primary amine, a secondary amine, or a tertiary amine. In some embodiments, one R of an amino group can be a cation stabilized diazeniumdiolate (i.e., NONO$^-$X$^+$).

The terms "cationic amine" and "quaternary amine" refer to an amino group having an additional (i.e., a fourth) group, for example a hydrogen or an alkyl group bonded to the nitrogen. Thus, cationic and quaternary amines carry a positive charge.

The term "alkylamine" refers to the -alkyl-NH$_2$ group.

The term "carbonyl" refers to the —(C=O)— group.

The term "carboxyl" refers to the —COOH group and the term "carboxylate" refers to an anion formed from a carboxyl group, i.e., —COO$^-$.

The terms "halo", "halide", or "halogen" as used herein refer to fluoro, chloro, bromo, and iodo groups.

The term "hydroxyl" and "hydroxy" refer to the —OH group.

The term "hydroxyalkyl" refers to an alkyl group substituted with an —OH group.

The term "mercapto" or "thio" refers to the —SH group.

The term "silyl" refers to a group comprising a silicon atom (Si).

As used herein the term "alkoxysilane" refers to a compound comprising one, two, three, or four alkoxy groups bonded to a silicon atom. For example, tetraalkoxysilane refers to Si(OR)$_4$, wherein R is alkyl. Each alkyl group can be the same or different. An "alkylsilane" refers to an alkoxysilane wherein one or more of the alkoxy groups has been replaced with an alkyl group. Thus, an alkylsilane comprises at least one alkyl-Si bond. The term "fluorinated silane" refers to an alkylsilane wherein one of the alkyl groups is substituted with one or more fluorine atoms. The term "cationic or anionic silane" refers to an alkylsilane wherein one of the alkyl groups is further substituted with an alkyl substituent that has a positive (i.e., cationic) or a negative (i.e. anionic) charge, or can become charged (i.e., is ionizable) in a particular environment (i.e., in vivo).

The term "silanol" refers to a Si—OH group.

The term "organic functional group" refers to any known organic functional groups, including all of the functional groups discussed above, either alone or in combination. The organic functional group may have any suitable valency. In some cases, organic functional groups are divalent, —R—, and in some cases, the organic functional groups are monovalent, —R.

Multi-Donor Compounds

Provided according to some embodiments of the invention are macromolecules that include at least two different nitric oxide (NO) donor structures of the same class. NO donors are of the same class if they have the same mechanism for release of nitric oxide. NO donors of the same class may be varied to provide different NO donor structures by altering the functional groups substituted on the NO donors. Accordingly, a nitric oxide donor structure as used herein includes at least one nitric oxide donor and at least one functional group substituted on the nitric oxide donor ("substituents") that together provide the complete nitric oxide donor structure and a signature NO-releasing behavior for that nitric oxide donor structure.

The functional group substituted on the NO donor can affect NO release kinetics of the NO donor structure. The inventors have discovered that combining different NO donor structures on a macromolecular framework can provide the ability to tune and/or vary the release rate of nitric oxide from the macromolecule based on the combination of the different NO donor structures. In particular, in some embodiments, the combination of different NO donor structures in a macromolecule can create a nano- or microenvironment that results in a distinct NO release profile, possibly as a result of an interaction of the effects of the different substituent functional groups of the NO donor structures. Such macromolecules may also be referred to herein as "multi-donor" macromolecules. The hydrophobicity/hydrophilicity, the steric bulk and the interaction of the different NO-donating structures with each other and/or other functional groups on the macromolecule are some of the factors which may affect the nitric oxide release rate. In some cases, the at least two different NO donor structures may be chosen to create a desired NO release profile for a particular use.

In some embodiments of the present invention, the combination of different NO donor structures of the same class on a macromolecule can result in a release profile of nitric oxide that is the weighted sum of the release profiles of the individual NO donor structures. However, in certain embodiments, the release profile of the macromolecule differs from the weighted sum of the release profiles of the individual NO donor structures. In such embodiments, release profiles that would not otherwise be achievable by combinations of NO releasing macromolecules with different NO donor structures may be realized.

In either of the above cases, the combination of different NO donor structures on a macromolecule may increase the predictability/probability that a given level of nitric oxide will be present at a given location over using a mix of macromolecules each with a single NO donor structures. For example, for a given unit volume containing a mixture of nitric oxide releasing small molecules having different release profiles, to achieve a desired release profile in a given location within the volume, the small molecules at that location must not only be of sufficient quantity but must also be of the correct types and in the correct proportions to achieve the release profile.

For the case where the volume contains a mixture of nitric oxide releasing macromolecules, the likelihood of achieving the local levels of nitric oxide may be increased as each macromolecule releases more nitric oxide and, therefore, fewer macromolecules need be at the given location to achieve the desired level of nitric oxide. Thus, even if the overall release levels of nitric oxide are lower, the localized NO release may be higher, thus allowing for smaller doses to achieve similar results. However, with a mixture of nitric oxide releasing macromolecules, the problem of having the correct proportion to achieve the desired profile at a given location may still be present.

By combining different NO donor structures on a macromolecule, the release profile for the macromolecule may be controlled such that any location within the volume will have the same or similar release profiles. In such a case, the only requirement to achieve the desired release profile at the given location is whether sufficient macromolecules are at the location to achieve the desired levels. However, as discussed above, the macromolecule also increases this likelihood at lower dose levels as each macromolecule would release higher levels of nitric oxide than would a small molecule NO donor.

In addition to providing performance benefits over mixtures of different nitric oxide releasing donors, the multi-donor macromolecule may also provide additional manufacturing benefits. For example, by creating a macromolecule with different NO donors, a single pharmaceutical composition may be provided with, in some embodiments, the characteristics of the constituent NO donors and, in other embodiments, a new characteristic different from that of any of the constituents. Thus, issues of mixture uniformity, batch variability and the like may be greatly reduced or eliminated.

In addition to allowing for the tuning and/or control of the release profile of an NO releasing macromolecule, utilizing different NO donor structures from the same class on a macromolecule may also improve the stability of the otherwise independent NO donor structure and/or the stability of the entire NO releasing macromolecule.

In some embodiments, the NO donor includes a diazeniumdiolate. Diazeniumdiolates react with proton donors to release NO at physiological pH (~7.4), and so the chemical functional groups that are substituted on the diazeniumdiolate donor may affect the ability of the diazeniumdiolate to react with the proton donors. Provided according to some embodiments of the invention are macromolecules that include at least two different diazeniumdiolate NO donor structures. In some cases, the at least two different diazeniumdiolate NO donor structures may be chosen to create a desired NO release profile for a particular use. Any suitable diazeniumdiolate NO donor structures may be used, including for example, C-based and N-based diazeniumdiolates, $O_2$-protected diazeniumdiolates, and the like.

In some embodiments, at least one of the diazeniumdiolate donor structures includes the formula —R—N(NONO$^-$ X$^+$)—R', wherein R is a divalent organic functional group, R' is a monovalent organic functional group, and X$^+$ is a monovalent cation. In some embodiments, R includes alkylene or arylalkylene, R' includes alkyl, substituted alkyl, alkylnitrile, aryl, substituted aryl, alkylaryl, polyether and/or alkylamine, and X$^+$ is includes Na$^+$ or K$^+$.

Examples of other NO donor classes include nitrosothiols, nitrosamines, hydroxyl nitrosamines, hydroxylamines, hydroxyureas, metal complexes, organic nitrites and organic nitrates.

As described above, embodiments of the invention provide an NO-releasing macromolecule. As used herein, a "macromolecule" is defined as having a molecular weight of 500 daltons or greater. Any suitable size of macromolecule may be used. However, in some embodiments of the invention, the hydrodynamic radius of the NO-releasing macromolecule is within a range from 0.01 nm to 1 nm, in some embodiments in a range from 1 nm to 10 µm, in some embodiments in a range from 101 nm to 1000 nm, and in some embodiments, in a range from 1000 nm to 10 µm. In some embodiments, the hydrodynamic radius is greater than 10 µm, in some embodiments, in a range from 10 µm to 100 µm, in some embodiments, greater than 100 µm, and in some embodiments, greater than 1000 µm.

Dendrimers

In some embodiments of the invention, the NO-releasing macromolecule includes a dendrimer. Any suitable dendrimer may be used, including, for example, polypropyleneimine (PPI) dendrimer; a polyamidoamine (PAMAM) dendrimer; polyarylether dendrimer; polypeptide dendrimer; polyamide dendrimer; dendritic polyglycerol; and triazine dendrimer.

Any suitable method may be used to synthesize the dendrimers. Particular dendrimers and methods for forming the same are described in detail in the examples below. Other methods of synthesizing dendrimers are known in the art, and may be used to form multi-donor dendrimers.

In some embodiments, the dendrimer includes at least two different diazeniumdiolate NO donor structures. In some cases, the dendrimer may include a relatively fast NO releasing diazeniumdiolate in combination with a relatively slow diazeniumdiolate. Moderate/fast and moderate/slow combinations may also be desirable in some cases. In particular embodiments, at least one of the diazeniumdiolate NO donor structures has a NO release half life that falls within a range from 30 seconds to 10 minutes and at least one diazeniumdiolate NO donor structure that has a NO release half life of greater than 60 minutes (e.g., that falls within a range from 60 minutes to 4 days), in an aqueous solution at pH 7.4 and 37° C. In some embodiments, at least one of the diazeniumdiolate NO donor structures has a NO release half life in a range from 30 seconds and 10 minutes and at least one diazeniumdiolate NO donor structure has a NO release half life greater than 10 minutes but less than or equal to 60 minutes, in an aqueous solution at pH 7.4 and 37° C. In some embodiments, at least one of the diazeniumdiolate NO donor structures has a NO release half life of more than 10 minutes but less than or equal to 60 minutes and at least one diazeniumdiolate NO donor structure has a NO release half life of greater than 60 minutes, in an aqueous solution at pH 7.4 and 37° C.

The maximum flux and NO release profile may also be varied in the multi-donor dendrimers, such that at least one of the diazeniumdiolate NO donor structures has a maximum flux of NO in a range from 2000 ppb NO/mg to 20,000 ppb NO/mg and a half life in a range from 0.1 to 1 hr, and at least one of the diazeniumdiolate NO donor structures has a maximum flux of NO in a range from 100 ppb NO/mg to 2000 ppb NO/mg and a half life in a range from 1 hr to 5 hr in an aqueous solution at pH 7.4 and 37° C. The structure, size, and hydrophobicity of the dendrimer can be varied to affect NO release.

As used herein, the values for the "NO release half life" and the "maximum flux" of a diazeniumdiolate NO donor structure are those of the corresponding dendrimer that includes only that diazeniumdiolate. It will be understood that these properties will be shifted in a multi-donor dendrimer due to the contribution of the other diazeniumdiolate NO donor structures.

In particular embodiments of the invention, the dendrimer includes at least one diazeniumdiolate NO donor structure having the structure:

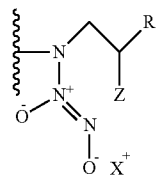

wherein R is —CN, —COO(CH$_2$CH$_2$O)$_{6-12}$H, —CH$_3$, —CH$_2$CH$_3$, -Ph, —C$_6$H$_{12}$CH=CH$_2$; Z is —H or —OH; and X is Na$^+$ or K$^+$.

Co-Condensed Silica

In some embodiments of the invention, the NO-releasing macromolecule includes co-condensed silica. Any suitable co-condensed silica having at least two different NO donor structures bound thereto may be used. The materials and methods that may be used to create NO-releasing co-condensed silica particles containing one nitric oxide donor structure throughout are described in U.S. Patent Application Publication No. 2009/0214618, the disclosure of which is incorporated by reference herein in its entirety. Examples of how to form multi-donor co-condensed silica are described below.

In some embodiments, each diazeniumdiolate NO donor structure may be formed from an aminoalkoxysilane by a pre-charging method, and the co-condensed siloxane network may be synthesized from the condensation of a silane mixture that includes an alkoxysilane and at least two different NO-loaded aminoalkoxysilanes to form a multi-donor co-condensed siloxane network. As used herein, the "pre-charging method" means that the aminoalkoxysilane is "pretreated" or "precharged" with nitric oxide prior to the co-condensation with alkoxysilane. In some embodiments, pre-charging with nitric oxide may be accomplished by chemical methods. In some embodiments, the "pre-charging" method can be used to create co-condensed siloxane networks and materials more densely functionalized with NO-donors.

The co-condensed siloxane network can be silica particles having a uniform size, a collection of silica particles with a variety of size, amorphous silica, a fumed silica, a nanocrystalline silica, ceramic silica, colloidal silica, a silica coating, a silica film, organically modified silica, mesoporous silica, silica gel, bioactive glass, or any suitable form or state of silica.

In some embodiments, the alkoxysilane is a tetraalkoxysilane having the formula Si(OR)$_4$, wherein R is an alkyl group. The R groups can be the same or different. In some embodiments the tetraalkoxysilane is selected as tetramethyl orthosilicate (TMOS) or tetraethyl orthosilicate (TEOS). In some embodiments, the aminoalkoxysilane has the formula: R"—(NH—R')$_n$—Si(OR)$_3$, wherein R is alkyl, R' is alkylene, branched alkylene, or aralkylene, n is 1 or 2, and R" is selected from the group consisting of alkyl, cycloalkyl, aryl, and alkylamine.

In some embodiments, the at least two different aminoalkoxysilanes are each independently selected from N-(6-aminohexyl)aminopropyltrimethoxysilane (AHAP3); N-(2-aminoethyl)-3-aminopropyltrimethoxysilane (AEAP3); (3-trimethoxysilylpropyl)di-ethylenetriamine (DET3); (aminoethylaminomethyl)phenethyltrimethoxysilane (AEMP3); [3-(methylamino)propyl]trimethoxysilane (MAP3); N-butylamino-propyltrimethoxysilane(n-BAP3); t-butylamino-propyltrimethoxysilane(t-BAP3); N-ethylaminoisobutyltrimethoxysilane (EAiB3); N-phenylamino-propyltrimethoxysilane (PAP3); and N-cyclohexylaminopropyltrimethoxysilane (cHAP3).

In some embodiments, at least one of the two different aminoalkoxysilane has the formula: NH [R'—Si(OR)$_3$]$_2$, wherein R is alkyl and R' is alkylene. In some embodiments, at least one of the aminoalkoxysilanes is selected from bis(3-triethoxysilylpropyl)amine, bis-[3-(trimethoxysilyl)propyl]amine and bis-[(3-trimethoxysilyl)propyl]ethylenediamine.

In some embodiments, as described herein above, the at least two different aminoalkoxysilanes are precharged, either together or separately, for NO-release and the amino group is substituted by a diazeniumdiolate. Therefore, in some embodiments, the aminoalkoxysilane has the formula: R"—N(NONO$^-$X$^+$)—R'—Si(OR)$_3$, wherein each R is independently H, alkyl, silyl or aryl, R' is a divalent organic functional group, R" is a monovalent organic functional group, and X$^+$ is a monovalent cation. In some embodiments, each R is independently methyl or ethyl, R' is alkylene or arylalkylene, R" is alkyl, substituted alkyl, alkylnitrile, aryl, substituted aryl, alkylaryl, polyether and/or alkylamine, and X$^+$ is a cation selected from the group consisting of Na$^+$, K$^+$, Cs$^+$, Li$^+$, NH$_4^+$, or other quaternary ammonium cation.

In some embodiments of the invention, one or more of the diazeniumdiolate-functional aminoalkoxysilanes may be $O^2$-protected prior to the preparation of the nitric oxide-releasing macromolecules. Such $O^2$-protected diazeniumdiolate functional aminoalkoxysilanes may have the formula: R"—N(NONO—R''')—R'—Si(OR)$_3$, wherein each R is independently H, alkyl, silyl or aryl, R' is a divalent organic functional group, R" is a monovalent organic functional group, and R''' is a protecting group that imparts enzymatic, photolytic, or thiolation triggering mechanisms. Such protecting groups are known to those skilled in the art of forming $O^2$-protected diazeniumdiolates.

The chemical composition of the siloxane network, (e.g., amount or the chemical composition of the aminoalkoxysilane), the porosity of the silica network within the macromolecular structure, the size of the co-condensed silica particles, and the nitric oxide charging conditions (e.g., the solvent and base) can be varied to optimize the amount and duration of nitric oxide release. Thus, in some embodiments, the composition of the silica particles can be modified to regulate the half-life of NO release from silica particles with half-lives of nitric oxide release ranging from slow, defined by $t_{1/2}$ values greater than 60 minutes, to moderate, defined by $t_{1/2}$ values greater than 10 minutes and less than or equal to 60 minutes, to fast, defined by $t_{1/2}$ values ranging from 30 seconds to 10 minutes. As described above, the combination of two or more different diazeniumdiolate NO donor structures may alter the $t_{1/2}$ values and the release profile.

In some embodiments, the multi-donor co-condensed silica may be present as particles. In some embodiments, the particles have a size distributed around a mean particle size of less than about 10 and in some embodiments, have a particle size distributed around a mean particle size of greater than about 10 μm, in some embodiments between 10 μm and 100 μm, in some embodiments greater than 100 μm, and in some embodiments greater than 1000 μm.

In some embodiments of the invention, the multi-donor co-condensed silica is also formed from at least one additional silane that modifies surface charge and/or hydrophilicity/hydrophobicity of the co-condensed silica product which affect the octanol/water partition coefficient of the macromolecular delivery vehicle. Any suitable alkoxysilane that may impart surface charge to the diazeniumdiolate-modified polysiloxane macromolecule may be used. Thus, in some embodiments, the additional alkoxysilane may include a cationic alkoxysilane such as (2-N-benyzlaminoethyl)-3-aminopropyltrimethoxysilane, hydrocholoride; bis(methoxyethyl)-3-trimethoxysilylpropyl-ammonium chloride; N—N-didecyl-N-methyl-N-(3-trimethoxysilyl) ammonium chloride; N-trimethyoxysilylpropyl-N,N,N-trimethyl ammonium chloride; octadecylbis(triethoxysilylpropyl)-ammonium chloride; and octadecyldimethyl(3-trimethoxysilylpropyl)ammonium chloride. In some embodiments, the additional alkoxysilane may include an anionic alkoxysilanes such as 3-trihydroxysilylpropylmethyl phosphonate, sodium salt and carboxyethylsilanetriol, sodium salt.

Any suitable alkoxysilane that may impart hydrophilic properties to the multi-donor co-condensed silica may be used. Alkoxysilanes containing repeat poly(ethylene)oxy groups may be used to increase the wetability of the NO-releasing particles thereby helping to improve biocompatibility upon topical application and also enhance the rate of water uptake into the co-condensed siloxane coating. Surface hydrophilicity can thus be utilized to enhance the NO-release kinetics of the diazeniumdiolated aminoalkoxysilane derivatives. Therefore, in some embodiments, the multifunctional alkoxysilane may include a hydrophilic silane such as N-triethoxysilylpropyl)-O-polyethyleneoxide urethane; N-3-[amino(polypropylenoxy)]aminopropyltrimethoxysilane; bis-[3-(triethoxysilylpropoxy)-2-hydroxypropoxy]polyethylene oxide; bis(3-triethoxysilylpropyl) polyethylene oxide (25-30); [hydroxy(polyethyleneoxy) propyl]-triethoxysilane; and 2-[methoxy(polyethyleneoxy) propyl]-trimethoxysilane.

Any suitable alkoxysilane that may impart hydrophobic properties to the multi-donor co-condensed silica may be used. Hydrophobic silanes are known to those skilled in the art to increase lipophilicity of particle surfaces. In some embodiments, the additional alkoxysilane may include linear alkyl, branched and cyclic alkylalkoxysilanes having at least three carbon atoms, substituted and unsubstituted phenyl alkoxysilanes, and fluorinated alkoxysilanes. Exemplary fluoroalkoxysilanes may include heptadecafluoro-1,1,2-2-tetrahydrodecyl)triethoxysilane (shown in FIG. 21), (3,3,3-trifluoropropyl)trimethoxysilane, (perfluoroalkyl)ethyltriethoxysilane, nonafluorohexyltrimethoxysilane, nonafluorohexyltriethoxysilane, (tridecafluoro-1,1,2,2-tetrahydrooctyl)triethoxysilane, and (tridecafluoro-1,1,2,2-tetrahydrooctyl)trimethoxysilane.

The hydrophilicity of the multi-donor co-condensed silica can be assessed by the use of a water/octanol partition coefficient. See *Octanol-Water Partition Coefficients: Fundamentals and Physical Chemistry, Vol. 2 of Wiley Series in Solution Chemistry*. Chichester: John Wiley & Sons Ltd. (1997), which is herein incorporated by reference in its entirety. For example, hydrophobic diazeniumdiolate-functionalized polysiloxane macromolecules may have a water/octanol partition coefficient in a range from 0.1 to 7, and hydrophilic diazeniumdiolate-functionalized polysiloxane macromolecules may have a water/octanol partition coefficient in a range from −2 to 0.

Other Macromolecular Scaffolds

Any other suitable NO-releasing macromolecular scaffold may be used, such as, for example, metallic clusters, including those described in U.S. Patent Application Publication No. 2009/0214618, the disclosure of which is incorporated by reference herein in its entirety. In other embodiments biodegradable macromolecular scaffolds may be used including, for example, chitosan, cellulose, and other polysaccharide materials.

Pharmaceutically Acceptable Compositions

In some embodiments, at least one NO-releasing macromolecule is present in a pharmaceutically acceptable composition. A pharmaceutically acceptable composition, as defined herein, refers to a composition that is suitable for application/delivery to a subject, such as a human, without undue side effects such as toxicity or irritation to the skin. Undue side effects are those that render the composition unsuitable for application/delivery to a subject because the harm from the side effects outweighs the benefits of the composition. In some embodiments, pharmaceutically acceptable compositions include at least one NO-releasing macromolecule; optionally, at least one additional therapeutic agent; and at least one pharmaceutically acceptable excipient.

The NO-releasing macromolecules may be present in pharmaceutically acceptable compositions according to embodiments of the invention at any suitable concentration, but in some embodiments, the NO-releasing macromolecules are present in the compositions at a concentration sufficient to achieve the therapeutic goal. For example, in some cases, the concentration is sufficient to reduce inflammation, promote healing and/or kill bacteria. As another example, in some cases, the concentration is sufficient to decrease, eliminate or prevent acne and/or decrease sebum production. In some embodiments, the concentration of NO-releasing macromolecules ranges from 0.1% to 20% w/w in the composition.

As described above, in some embodiments, pharmaceutically acceptable compositions include at least one additional therapeutic agent, such as those that have antimicrobial, anti-inflammatory, pain-relieving, immunosuppressant, vasodilating properties.

Pharmaceutically acceptable compositions in which the present multi-donor NO releasing macromolecule may be utilized include those as described in U.S. application Ser. No. 12/580,418, filed Oct. 16, 2009; U.S. application Ser. No. 12/860,657, filed on Aug. 20, 2010; U.S. application Ser. No. 12/860,457, filed Aug. 20, 2010; and U.S. Provisional Patent Application No. 61/504,628; filed Jul. 5, 2011, the contents of each of which are hereby incorporated by reference in their entirety.

Methods of Treatment Using Compositions of the Invention

Provided according to embodiments of the invention are methods of treating a subject by administering to the subject a macromolecule or a pharmaceutical composition according to an embodiment of the invention. NO has been shown to be beneficial for the treatment of many medical conditions. As such, any suitable medical condition may be treated with a composition of the invention. In particular, the compositions described herein may be beneficial for the treatment of dermatological conditions. Examples include microbial infections, inflammation, wounds, scars, acne, and the like. Other conditions are discussed in U.S. Publication No. 2009/0214618, which contents are incorporated by reference in their entirety. Dermatological conditions are also discussed in U.S. Provisional Patent Application No. 61/504,634; filed Jul. 5, 2011, the contents of which are herein incorporated by reference in their entirety.

In some embodiments, the pharmaceutically acceptable composition according to embodiments of the invention may be applied topically to the skin of the subject. Any portion of the subject's skin may be treated. However, in some embodiments, the subject's face is treated by a method described herein. Furthermore, in some embodiments, the subject's trunk is treated by a method described herein.

Additionally, in some embodiments, the pharmaceutically acceptable composition according to embodiments of the invention is applied in another manner, such as systemic application. As used herein, systemic application refers to application/delivery of the pharmaceutically acceptable composition throughout the body. Furthermore, in some embodiments, the pharmaceutically acceptable composition may be applied/delivered to the subject parenterally, orally, buccally, subcutaneously, via inhalation, intratracheally, surgically, transdermally, or by any other method known in the art for introduction of a medicament to the body.

Subjects suitable to be treated with a method embodiment of the invention include, but are not limited to, avian and mammalian subjects. Mammals of the present invention include, but are not limited to, canines, felines, bovines, caprines, equines, ovines, porcines, rodents (e.g. rats and mice), lagomorphs, primates, humans, and the like, and mammals in utero. Any mammalian subject in need of being treated according to the present invention is suitable. Human subjects of both genders and at any stage of development (i.e., neonate, infant, juvenile, adolescent, adult) can be treated according to the present invention.

Illustrative avians according to the present invention include chickens, ducks, turkeys, geese, quail, pheasant, ratites (e.g., ostrich) and domesticated birds (e.g., parrots and canaries), and birds in ovo.

The invention can also be carried out on animal subjects, particularly mammalian subjects such as mice, rats, dogs, cats, livestock and horses for veterinary purposes, and for drug screening and drug development purposes.

In some embodiments, methods of treating a dermatological condition by administering to a subject a pharmaceutical composition according to an embodiment of the invention may be performed in combination with another therapeutic regimen and/or in combination with other medicaments, such as those that have antimicrobial, anti-inflammatory, pain-relieving, immunosuppressant, vasodilating properties, and/or anti-acne properties. For example, in the treatment of acne, other anti-acne agents such as retenoids, may be used in conjunction (prior, concurrently or after) with the application of the pharmaceutical composition of the invention. As such, in some embodiments of the invention, a patient may be treated with a composition described herein in combination with an additional therapeutic agent when the additional therapeutic agent is not in the same composition. For example, in some embodiments, an additional therapeutic agent may be administered (e.g., topically, systemically, parenterally, orally, buccally, subcutaneously, via inhalation, intratracheally, surgically, transdermally, etc.), either concurrently and/or sequentially with application of the pharmaceutically acceptable composition.

In some embodiments of the invention, a pharmaceutically acceptable composition may be administered to the skin via spray delivery. A non-aqueous delivery propellant may be used for water sensitive NO-releasing compounds such as diazeniumdiolate-modified compounds. Further, in some embodiments, particular components of the medicaments may be separated at some point prior to application of the medicament. For example, a water reactive NO-releasing compound may be stored separately from an aqueous component or propellant until application (e.g., via spraying or applying a gel). In some embodiments, the NO-releasing compounds may be combined with an aqueous constituent prior to application or the NO-releasing compounds and an aqueous constituent may be applied to the skin sequentially.

In some embodiments, a composition that includes nitrosothiol-modified compounds may be kept at a low temperature (e.g, <0° C.) to minimize thermal decomposition and NO release. The cold composition may then be applied to the skin, and the elevated temperature of the skin may allow for the release of NO. In some embodiments, the nitrosothiol may be present in a medicament (e.g., a hydrophilic formulation which may limit NO diffusion) such that it is stable at room temperature due to cage effects, and then releases NO upon application to the skin. Light may also be applied to a medicament that includes nitrosothiol modified compounds. The application of light in fluxes may be applied to create fluxes of NO.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The present invention will be further illustrated by the following non-limiting examples.

EXAMPLES

Dendrimers: Materials and General Considerations

Ethylenediamine (EDA), acrylonitrile (ACN), propylene oxide (PO), styrene oxide (SO), methyl acrylate (MA), poly(ethylene glycol) methyl ether acrylate (average Mn=480) (PEG), and 1,2-epoxy-9-decene (ED) were purchased from Aldrich Chemical Company (Milwaukee, Wis.). 1,6-Hexanediamine (HDA) and sodium methoxide (5.4 M solution in methanol) was purchased from Acros Organics (Geel, Belgium). Matthey Catalysts (London, UK). Common laboratory salts and solvents were purchased from Fisher Scientific (Pittsburgh, Pa.). All other materials were used as received without further purification unless otherwise noted. 1H nuclear magnetic resonance (NMR) spectra were recorded on Bruker (400 MHz) and Varian (600 MHz) spectrometers. Hydrogenation reactions used for the synthesis of PPI-NH2 (e.g., from G2 to G5) were carried out in a stainless steel high-pressure reactor purchased from Parr Instrument Company (Moline, Ill.). Agitation was provided by a Teflon-coated magnetic stirring bar. Heating was provided using a heating fabric wrapped around the reactor, and temperature was controlled using a temperature controller via a thermal coupler. Nitric oxide release was measured using Sievers 280i Chemiluminesce Nitric Oxide Analyzer (Boulder, Colo.).

Example 1: Synthesis of [G-0.5]-PPI-CN to [G-4.5]-PPI-CN

For the synthesis of [G-0.5]-PPI-CN, ethylenediamine (EDA, 25.0 mL, 0.374 mol) and deionized water (263 mL) were placed in a 1000 mL round-bottomed flask. Acrylonitrile (ACN, 140 mL) was added in portions of 20 mL with stirring for 15 min. The resulting mixture was refluxed for 2 h, and then cooled to room temperature overnight. ACN was removed in vacuo at 40° C. [G-0.5]-PPI-CN was crystallized from the mixture and isolated by vacuum filtration. The crude product was recrystallized from THF/methanol as a white powder.

Representative 1HNMR data was as follows: (300 MHz, CDCl3): δ (ppm) 2.55 (8H, NCH2CH2CN), 2.77 (4H, —NCH2CH2N—), 2.96 (t, 8H, —NCH2CH2CN). Synthesis of higher generation PPI-CN (e.g., from [G-1.5] to [G-4.5]) was not significantly different from the synthesis of PPI-[G-0.5]-CN as described above, with the exception that PPI-CN (e.g., from [G-1.5] to [G-4.5]) were usually viscous liquids and their purification processes would normally require the use of preparative-scale chromatography. As a result, the synthesis of higher generation PPI-CN was conducted in a modified manner. Higher generation PPI-CN (10.0 g) (e.g., from [G-1.5] to [G-4.5]) was dissolved in deionized water (50 mL) and THF (100 mL) prior to adding ACN (50 mL). If phase separation of the resulting solution was observed, an additional amount of THF was added. The reaction mixture was stirred at room temperature for 3 d; a small amount was then removed for analysis by 1H NMR spectroscopy to determine the extent of reaction. If the reaction was incomplete, an additional amount of ACN (25 mL) was added stirring continued for 2-3 additional days.

Example 2: Synthesis of [G-1]-PPI-NH2 to [G-5]-PPI-NH2

For the synthesis of [G-1]-PPINH2, sponge cobalt catalyst (5.0-6.0 g) was washed with 10% KOH solution for 10 min, three times with de-ionized water, and twice with methanol prior to use. [G-0.5]-PPI-CN (10.0 g) was placed in a glass reactor sleeve and dissolved in THF (70 mL) and methanol (30 mL). To this solution, the sponge cobalt catalyst prepared as described above (5.0-6.0 g) was added using a pipet. The reactor sleeve was then placed in the hydrogenation chamber with proper stirring. The reactor was purged with house nitrogen (60 PSI) five times, and then with hydrogen (400 PSI) twice. The reactor was charged with hydrogen to a pressure of 800 PSI, and heated to 100° C. The hydrogen gas pressure was maintained at 1000 PSI throughout the reaction. After 3 h, the reaction mixture was cooled to room temperature. Hydrogen was slowly removed, and the reaction chamber was purged once with house nitrogen. The resulting reaction mixture was then filtered to remove the cobalt catalyst, and solvent was removed in vacuo. The final product was dried under vacuum overnight to yield [G-1]-PPI-NH2 as a colorless liquid.

Representative 1H-NMR data was as follows: (300 MHz, CDCl3): δ (ppm) 1.52 (q, 8H, NH2CH2CH2CH2N—), 2.40 (t, 8H, NH2CH2CH2CH2N—), 2.44 (s, 4H, —NCH2CH2N—), 2.64 (t, 8H, NH2CH2CH2CH2N—). The approach to synthesis of higher generation PPI-NH2 (e.g., from [G-2] to [G-5]) was similar to that of [G-1]-PPI-NH2 with the exception that a mixture of EDA and THF (50:50, v/v) was used as a solvent. After reaction, the solvent was removed in vacuo using 1-butanol as an azeotropic agent due to its high boiling point. The resulting higher generation PPI-NH2 (e.g., from [G-2] to [G-5]) was dried under vacuum overnight to yield a light yellow liquid. Mass analysis by ESI MS was as follows: 744.73, 1657.64, 3483.45 and 7142.4 for G2-PPI, G3-PPI, G4-PPI and G5-PPI, respectively.

Example 3: Synthesis of Secondary Amine-Functionalized PPI Dendrimers 100 mg PPINH$_2$ (e.g., from G2 to G5) was dissolved in 2 ml methanol in a 10 ml vial. One equivalent of acrylonitrile (ACN), poly(ethylene glycol) methyl ether acrylate (average Mn=480) (PEG), propylene oxide (PO), styrene oxide (SO), or 1,2-epoxy-9-decene (ED) (e.g., with respect to molar amount of primary amine functionality) was then added to the 10 mL vial. The solution was stirred at room temperature for 4 days. Solvent was removed under reduced pressure. Dendrimers were dissolved in water followed by dialysis against water and lyophilization.

Representative 1H NMR data of secondary amine-functionalized G5-PPI conjugate formed via the reactions of G5-PPI-NI-1$_2$ with ACN, PEG, PO, SO, and ED (referred to hereafter as G5-PPI-ACN a-64, G5-PPI-PEG b-64, G5-PPI-PO c-64, G5-PPI-SO d-64, G5-PPI-ED e-64) were as follows: G5-PPI-ACN a-64: 1H NMR (400 MHz. CD3OD, δ): 2.87 (NHCH2CH2CN), 2.82 (NHCH2CH2CN), 2.60 (NCH2CH2CH2NH), 2.40 (NCH2CH2CH2NH), 1.60 (NCH2CH2CH2NH). 13C NMR (400 MHz, CD3OD, δ): 117, 52.4, 51.8, 44.5, 33.3, 26.1, 23.6, 16.9. G5-PPI-PEG b-64: 1H NMR (400 MHz, CD3OD, δ): 2.60 (NCH2CH2CH2NH), 2.40 (NCH2CH2CH2NH), 1.60 (NCH2CH2CH2NH), 3.40-330 (OCH2CH2O), 2.80 (CH2NHCH2CHCOOPEG), 2.65 (CH2NHCH2CHCOOPEG), 2.42 (CH2NHCH2CHCOOPEG). 13C NMR (400 MHz, CD3OD, δ): 172, 71.6, 70.85, 69.3, 60.1, 57.0, 51.4, 43.9, 39.1, 22.9. G5-PPI-PO c-64: 1H NMR (400 MHz, CD3OD, δ): 3.70 (CH2CH(OH)CH3), 2.60-2.62 (CH2CH(OH)CH3, NCH2CH2CH2NH), 2.40 (NCH2CH2CH2NH), 1.60 (NCH2CH2CH2NH), 1.00 (CH2CH(OH)CH3). 13C NMR (400 MHz, CD3OD, δ): 66.9, 58.2, 53.7, 52.8, 41.2, 30.8, 27.6, 24.9, 21.8. G5-PPI-SO d-64: 1H NMR (400 MHz, CD3OD, δ): 7.50-7.20 (CH2CH(OH)Ph), 3.70 (CH2CH (OH)Ph), 2.72 (CH2CH(OH)Ph), 2.60 (NCH2CH2CH2NH), 2.40 (NCH2CH2CH2NH), 1.60 (NCH2CH2CH2NH). 13C NMR (400 MHz, CD3OD, δ): 140.6, 128.2, 127.5, 127.3, 125.8, 71.9, 57.1, 52.4, 45.6, 39.8, 26.3, 23.6. G5-PPI-ED e-64: 1H NMR (400 MHz, CD3OD, δ): 5.74 (CH2CH═CH2), 4.88 (CH2CH═CH2), 3.58 (NHCH2CH(OH)CH2), 2.60 (NCH2CH2CH2NH), 2.40 (NCH2CH2CH2NH), 1.98 (CH2CH═CH2), 1.60 (NCH2CH2CH2NH), 1.2-1.4 ((CH2)5CH2CH═CH2). 13C NMR (400 MHz, CD3OD, δ): 140.0, 116.1, 70.5, 56.5, 52.4, 47.2, 39.2, 33.9, 30.2, 25.6, 24.9.

Example 4: Synthesis of N-Diazeniumdiolate-Functionalized PPI Dendrimers

One equivalent of 5.4 M sodium methoxide solution in methanol (e.g., with respect to the molar amount of primary amine functionalities in PPI-NH2 used to synthesize these secondary amine-functionalized PPI) was added to a vial containing G1 to G5 secondary amine-functionalized PPI dendrimers in methanol (2 mL). The resulting reaction solution was charged with 10 atm of NO while stirring in a stainless steel reactor. Prior to charging with NO, the reactor was flushed three times with argon followed by a series of three longer charge/discharge cycles with argon (3×10 min) to remove oxygen from the stirring solutions. The reactor was then filled with 10 atm of NO (purified over KOH pellets for 30 min to remove trace NO degradation procedures described above with argon to remove unreacted NO from the reaction solution products) at ambient temperature. After 3 days, the NO was expunged using the same charge/discharge

Example 5: Characterization of NO Storage and Release

Aliquots (~10-25 μL) of N-diazeniumdiolate-functionalized PPI as a solution in methanol (e.g., ~7-200 mM) were added to 30 mL phosphate buffered saline (PBS) (10 mM, pH=7.4) at 37° C. to initiate/measure NO release. Chemiluminescence data for the NO-releasing dendrimers were represented as: i) total amount of NO release (t[NO], μmol NO/mg and μmol NO/μmol of secondary amine-functionalized dendrimers); ii) maximum flux of NO release ([NO] max, ppb/mg of secondary amine-functionalized dendrimers); iii) half-life (t1/2) of NO release; and, iv) conversion efficiency defined as percentages of amine functionalities in PPI (e.g., from G1 to G5) converted to N-diazeniumdiolate functionality (e.g., total moles of NO release divided by twice the molar amount of primary amine functionalities in PPI-NH2 used initially to synthesize secondary amine-functionalized dendrimer conjugates).

Dendrimer Results and Discussion

Chemical reactions of primary amine functionalities with organic compounds are considered to be the most straightforward approach for preparing secondary amine-containing compounds. Both the ring-opening reactions of primary amine-containing compounds with epoxides and conjugate-addition reactions of primary amine functionalities with α,β-unsaturated double bonds represent viable approaches for designing secondary amine-functionalized PPI conjugates. We thus targeted the synthesis of secondary amine-functionalized dendrimers using ring-opening and conjugate-addition reactions of PPI-NH$_2$ with PO, SO, ED, ACN and PEG (See FIG. 1).

The epoxides, acrylates and acrylonitrile used for conjugation were based on sterics, hydrophobicity and biocompatibility. Of note, it is also possible to yield tertiary amine adducts. In addition, we carried out a series of model kinetic studies using NMR spectroscopy for conjugate-addition reactions of first generation G1-PPI-NH$_2$ with ACN, 1,6-hexanediamine (HDA) with MA, and ring-opening reactions of HDA with PO to determine the suitability of conjugate-addition and ring-opening reactions for the synthesis of secondary amine-functionalized PPI dendrimers. The results of these studies revealed large differences in the rates of reactions of G-1-PPI-NH$_2$ with ACN, and HDA with PO. The rate constants of the first conjugate-addition or ring-opening reaction (k$_1$) were substantially larger than those of the second reactions (k$_2$) (data not shown), providing strong support for the use of such reactions (e.g., over a period of four days, in a dilute solution, and at one equivalent of ACN, epoxides, or acrylates with respect to molar amount of PPI-NH$_2$) to yield secondary amine-functionalized products suitable for subsequent NO release studies.

The approach described above is based on dendrimer functionalization at their exterior to yield secondary amine-functionalized PPI dendrimers. A practical advantage of this approach is that the synthesis of structurally diverse secondary amine-functionalized dendrimers may allow the identification of key properties for NO storage and release. Indeed, reactions of secondary amine-functionalized PPI (e.g., from G2 to G5) with NO under basic conditions (e.g., sodium methoxide) yielded N-diazeniumdiolate NO donor-functionalized dendrimers with diverse NO release characteristics.

Figure 2A:
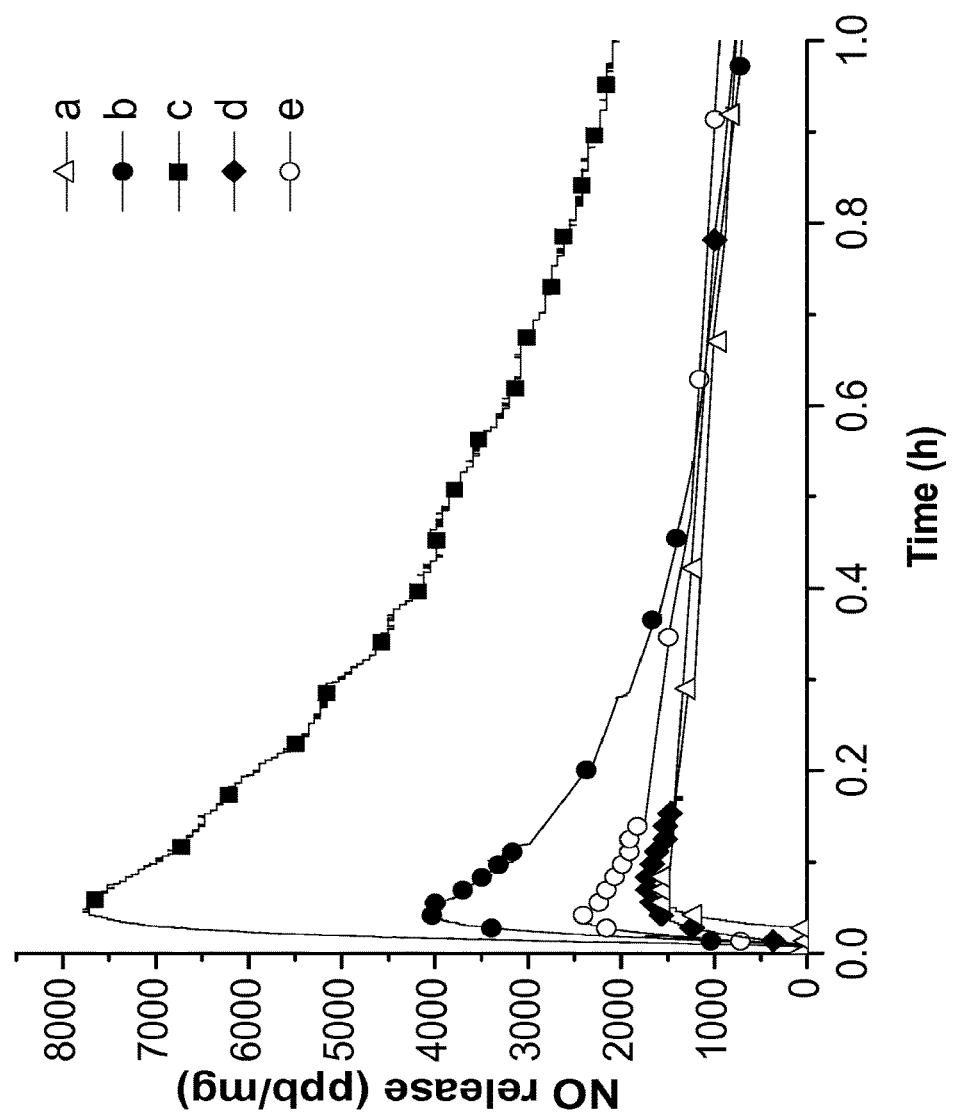
FIGS. 2A and 2B are graphs that provide (2A) a real time NO release profile for NO-releasing G4-PPI dendrimer conjugates; and (2B) a plot of t[NO] vs time for NO-releasing PPI dendrimer conjugates.
Figure 2B:
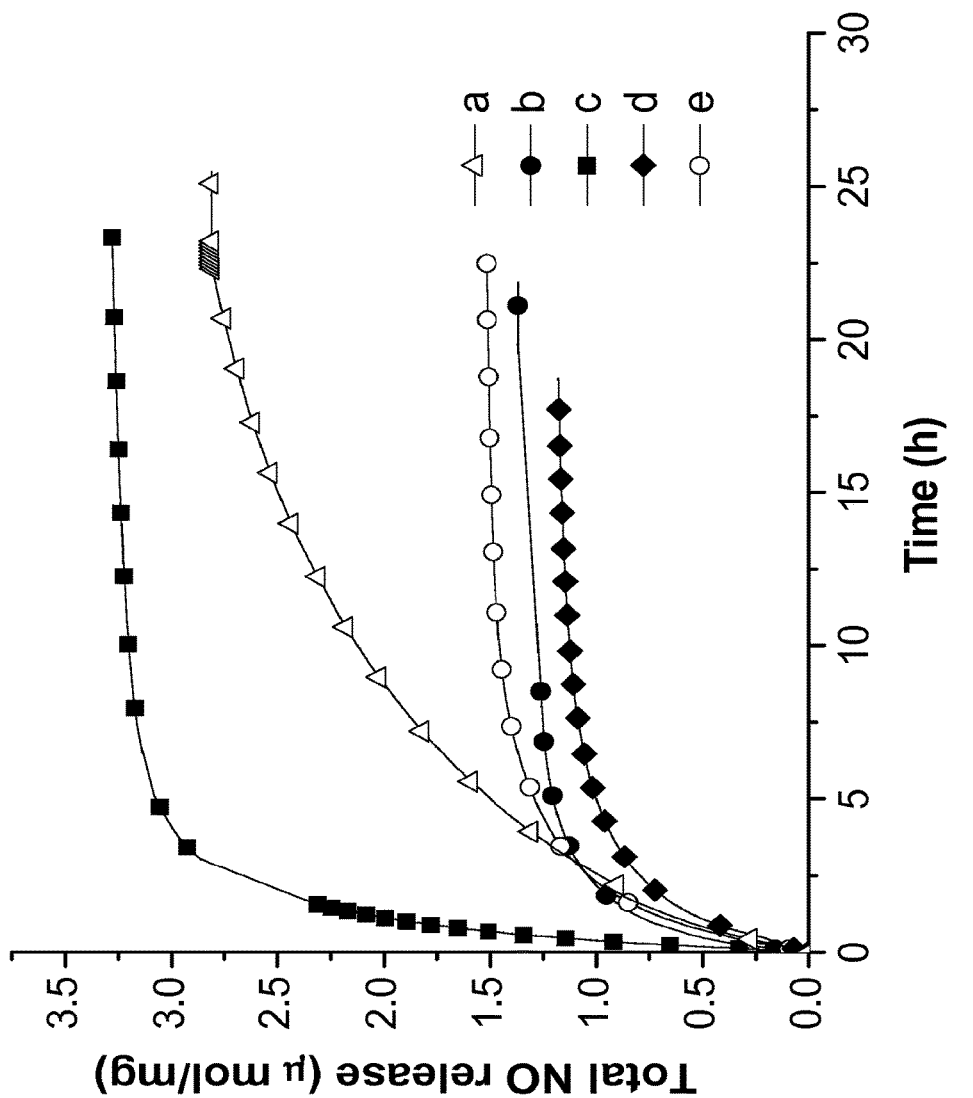

Chemiluminescence was used to characterize the NO storage and release properties (e.g., in PBS, pH=7.4, 37° C.) for the N-diazenuimdiolate-modified PPI dendrimers. Representative NO release profiles for these dendrimers are shown in FIGS. 2A and 2B. The workup of specific NO release parameters (e.g., total NO release, maximum flux, half-life and conversion efficiency) are provided in Table 1. In general, the NO release results reveal high NO storage capabilities (e.g., 0.9-3.8 μmol NO/mg) and a broad range of release kinetics (e.g., NO release half-life from 0.8-4.9 h). Further inspection of these data reveals that the conversion efficiencies (e.g., 10-34%) of the dendrimers varied substantially based on the chemical modification. As shown in Table 1, G2 to G5-PPI-SO (d-n-NO) were characterized by lower NO donor formation (e.g., ~10-15%) versus the other PPI dendrimers (e.g., ~14-40%). The lower conversion efficiencies for PPI-SO (d-n-NO) may be attributed to a more sterically-hindered environment around the NO donor precursors (i.e., secondary amines), resulting in lower NO and base accessibility to the amines during the NO charging process.

TABLE 1

Nitric oxide release characteristics for PPI dendrimers in PBS (pH = 7.4) at 37° C.

| | Dendrimer | t[NO] (μmol NO/mg)[a] | t[NO] (μmol NO/μmol)[b] | [NO]$_{max}$ (ppb/mg)[c] | [NO]$_{max}$ (ppb/μmol)[d] | t$_{1/2}$(h) | Conversion (%) |
|---|---|---|---|---|---|---|---|
| a-8-NO | G2-PPI-ACN-NO | 3.57 | 4.18 | 1529 | 1788 | 4.81 | 26.1 |
| a-16-NO | G3-PPI-ACN-NO | 3.33 | 8.35 | 1100 | 2758 | 4.84 | 26.1 |

TABLE 1-continued

Nitric oxide release characteristics for PPI dendrimers in PBS (pH = 7.4) at 37° C.

| | Dendrimer | t[NO] (μmol NO/mg)$^a$ | t[NO] (μmol NO/μmol)$^b$ | [NO]$_{max}$ (ppb/mg)$^c$ | [NO]$_{max}$ (ppb/μmol)$^d$ | $t_{1/2}$(h) | Conversion (%) |
|---|---|---|---|---|---|---|---|
| a-32-NO | G4-PPI-ACN-NO | 2.45 | 12.7 | 1547 | 7977 | 4.82 | 19.9 |
| a-64-NO | G5-PPI-ACN-NO | 1.68 | 17.7 | 881 | 9282 | 4.88 | 13.8 |
| b-8-NO | G2-PPI-PEG-NO | 1.11 | 5.10 | 3771 | 17291 | 0.67 | 31.9 |
| b-16-NO | G3-PPI-PEG-NO | 1.08 | 10.1 | 2309 | 21564 | 1.11 | 31.6 |
| b-32-NO | G4-PPI-PEG-NO | 1.37 | 25.8 | 4088 | 77035 | 0.84 | 40.3 |
| b-64-NO | G5-PPI-PEG-NO | 1.17 | 44.3 | 1886 | 71403 | 1.22 | 34.6 |
| c-8-NO | G2-PPI-PO-NO | 2.99 | 3.63 | 17130 | 20725 | 0.30 | 22.7 |
| c-16-NO | G3-PPI-PO-NO | 3.22 | 8.38 | 9617 | 24888 | 0.62 | 26.2 |
| c-32-NO | G4-PPI-PO-NO | 3.27 | 17.5 | 7762 | 41481 | 0.78 | 27.3 |
| c-64-NO | G5-PPI-PO-NO | 3.78 | 41.1 | 6839 | 74250 | 1.06 | 32.1 |
| d-8-NO | G2-PPI-SO-NO | 1.14 | 1.95 | 8495 | 14496 | 1.47 | 12.2 |
| d-16-NO | G3-PPI-SO-NO | 0.91 | 3.30 | 2363 | 8462 | 0.97 | 10.3 |
| d-32-NO | G4-PPI-SO-NO | 1.18 | 8.70 | 1720 | 12609 | 1.43 | 13.6 |
| d-64-NO | G5-PPI-SO-NO | 1.25 | 18.5 | 3315 | 32843 | 1.62 | 14.5 |
| e-8-NO | G2-PPI-ED-NO | 1.95 | 3.87 | 5648 | 11178 | 0.81 | 24.2 |
| e-16-NO | G3-PPI-ED-NO | 1.64 | 6.75 | 2733 | 11279 | 1.71 | 21.1 |
| e-32-NO | G4-PPI-ED-NO | 1.51 | 12.8 | 2401 | 20217 | 1.34 | 19.9 |
| e-64-NO | G5-PPI-ED-NO | 1.86 | 31.6 | 3190 | 54262 | 1.88 | 24.7 |

$^a$total amount of NO release (μmol) per milligram of secondary amine-functionalized PPI.
$^b$total amount of NO release (μmol) per micromole of secondary amine-functionalized PPI.
$^c$maximum flux of NO release (ppb) per milligram of secondary amine-functionalized PPI.
$^d$maximum flux of NO release (ppb) per micromole of secondary amine-functionalized PPI.

The exterior modification also influenced the NO release kinetics. For example, both PPI-PO (c-n-NO) and PPI-PEG (b-n-NO) released NO rapidly (Table 1 and FIGS. 2A-2B). Isopropyl and PEG groups are hydrophilic and facilitate water salvation that can be favorable to diazeniumdiolate NO donor degradation, so these groups could provide for rapid NO release kinetics. The data also indicate that the NO release half-lives for G2-G5 PPI-SO (d-n-NO) and PPI-ED (e-n-NO) are slightly longer than PPI-PO (c-n-NO) and PPI-PEG (b-n-NO). The longer NO release for PPI-SO (d-n-NO) and PPI-ED (e-n-NO) correlates well with the increased hydrophobic structure at the exteriors of these dendrimers.

The ACN modification for PPI dendrimer (a-n-NO) exhibited large NO storage (e.g., ~4.7-3.6 μmol NO/mg) and conversion efficiency (e.g., ~14-26%) (Table 1). Of note, past studies have indicated that the reaction of cyano-containing compounds with NO at high-pressures under basic conditions may yield C-diazeniumdiolate-functionalized products. Both NO and nitrous oxide (N$_2$O) may be release from C-diazeniumdiolates in aqueous environments at low pH. In this context, it may be possible that the high conversion efficiencies for PPI-ACN (a-n-NO) arise from the contribution of NO released from C-diazeniumdiolate-functionalized products. A series of experiments were thus carried out to probe the nature of the NO release from PPI-ACN (a-n-NO) using G0.5-PPI, a cyano-containing compound without the capacity to form N-diazeniumdiolate due to the absence of secondary amines. The NO release from G0.5-PPI was ~4.5×10$^{-3}$ μmol NO/mg, providing strong support that the high NO storage and conversion efficiency for the ACN-modified dendrimers are indeed the result of N-diazeniumdiolate functionalization.

The PPI-ACN (a-n-NO) analogues were also characterized as having the longest NO release half-lives (e.g., ~5 h). Given the hydrophilic nature of the cyano functionality, the extended NO release is not easily attributed to water uptake. For example, the long half-lives of N-diazeniumdiolate-functionalized small molecule derivatives (e.g., dipropylen-etriamine or DPTA-NO) have previously been attributed to diazeniumdiolate stabilization by neighboring cationic ammonium functionalities as depicted in molecules A and B below.

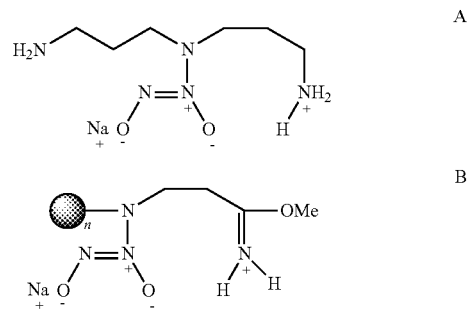

In this manner, the presence of neighboring cationic functionalities (e.g., protonated imidates) for PPI-ACN (a-n-NO) dendrimers may provide additional stabilization to the diazeniumdiolate functionality (A). Since sodium methoxide was used as the base for the reaction of PPI-ACN (a-n) with NO (to yield diazeniumdiloate-functionalized products), the methoxide anion may also serve as a nucleophile to react with the cyano group in PPI-ACN (a-n) and yield imidate adducts.[53] The transfer of proton from solvent (e.g., methanol) to the relatively basic nitrogen atom in the resulting imidates might thus lead to protonated-imidate functionality (B) that is similar to cationic ammonium functionality in DPTA-NO (A).

As shown in Table 1, both the NO storage and maximum NO flux per dendrimer molecule increase as a function of dendrimer size (i.e., generation). For example, the NO payload from G5-PPI-PO-NO (c-64-NO) was 41.1 μmol/μmol dendrimer, much greater than G2-PPI-PO-NO (c-8-NO) (e.g., 3.63 μmol/μmol dendrimer). A similar trend is observed for maximum NO flux. These results reveal the capability of larger NO-releasing PPI dendrimers to deliver significant concentrations of NO. As synthesized, the amphiphilic secondary amine-functionalized dendrimers (e.g., PPI-SO, PPI-ED) possess a hydrophilic PPI core and hydrophobic periphery of aromatic rings or long alkyl chains. Different from PPI-ACN, PPI-PO and PPI-PEG, these amphiphilic dendrimers may have more packed exterior in the charging solvent due to the poor compatibility of the aromatic rings or long alkyl chains with polar solvent (e.g., methanol).

Figure 3:
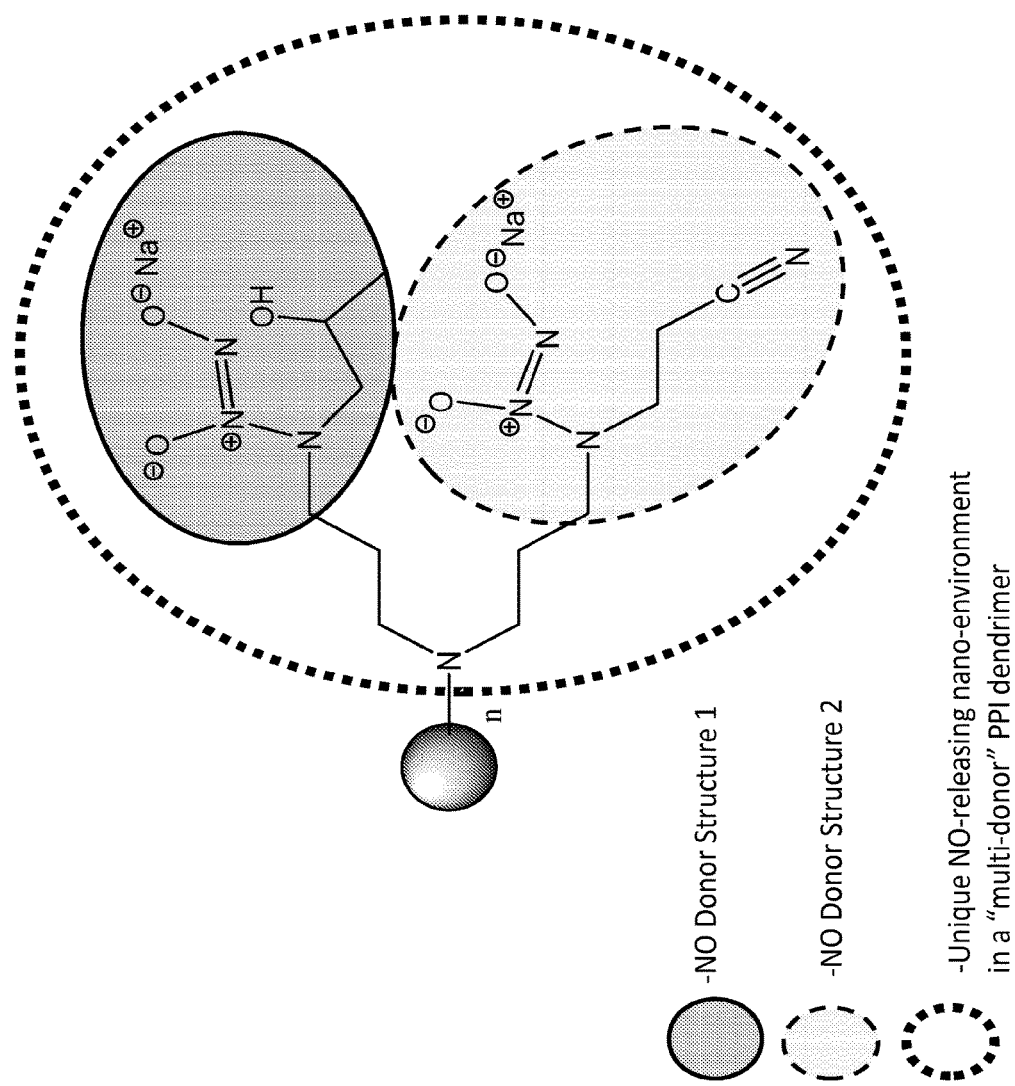
FIG. 3 is a schematic illustrating diazeniumdiolate-modified G5-PPI-PO/ACN (n=32) and it depicts the structurally different NO donor groups and the surrounding nano environment of the "multi-donor" system (shown in a 1:1 ratio as an example).

To evaluate the ability to create tunable NO release profiles between the release kinetics observed for single PPI dendrimer modifications, we designed multi-functionalized N-diazeniumdiolate-functionalized dendrimer conjugates using G5-PPI-NH$_2$ with defined ratios of PO and/or ACN at the exterior. Specifically, G5-PPI-NH$_2$ was reacted with either PO exclusively (e.g., c-64), ACN exclusively (e.g., a-64), or three different mixtures comprised of PO and ACN at molar ratios of 3:7, 5:5, and 7:3, respectively; the PO, ACN, or defined mixtures of PO and ACN were one equivalent with respect to molar amount of primary amine functionalities in G5-PPI-NH$_2$. FIG. 3 illustrates that the two donor structures may interact to form a unique NO-releasing nano-environment.

Figure 4:
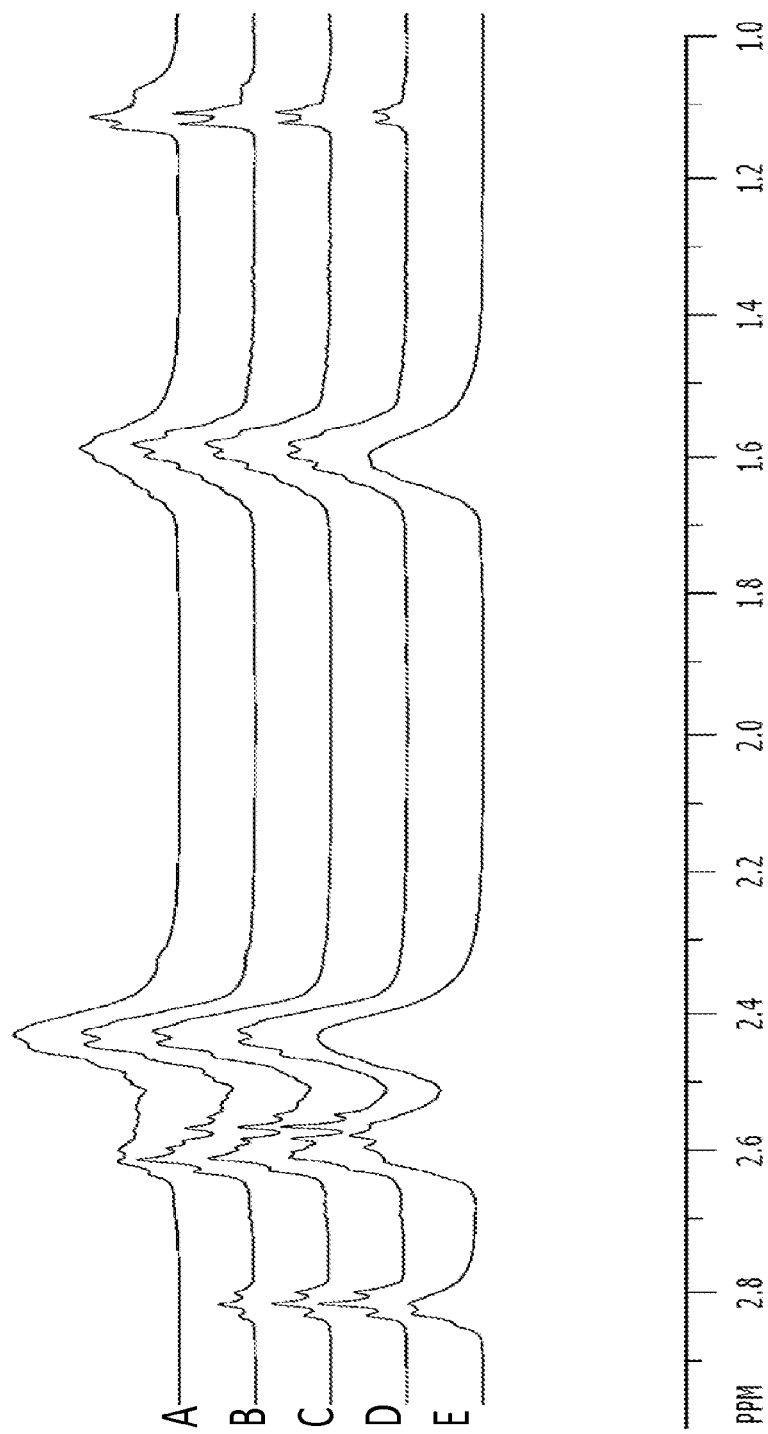
FIG. 4 provides an 1H NMR spectra of G5-PPI-PO (c-64) (A), G5-PPI-ACN (a-64) (E), G5-PPI-PO/ACN at molar ratios of 7:3 (B), 5:5 (C), and 3:7 (D). The actual compositions of PO and ACN incorporated into these three PPI conjugates are at molar ratios of 27:73 (B), 40:60 (C) and 60:40 (D) respectively, as determined by integrating two chemical shifts at 1.10 and 2.80 ppm.

A series of $^1$H NMR experiments were carried out on the products of these reactions to determine the actual compositions of PO and ACN conjugated to the G5-PPI-NH$_2$ (FIG. 4). A distinct resonance at 1.10 ppm was apparent corresponding to the methyl protons in the isopropyl group of the products. The chemical shift of this peak was noted in the products for reactions with PO exclusively (e.g., c-64) and those with different mixtures of PO and ACN. Further inspection of these data indicates the presence of a second distinct peak at 2.80 ppm, formed upon G5-PPI-NH$_2$ dendrimer reaction with either ACN exclusively (e.g., a-64) or defined mixtures of PO and ACN; this peak corresponds to the methylene protons one carbon away from the cyano group of the products. The compositions of PO and ACN incorporated in the products were 27/73 (c/a (27/73)), 40/60 (c/a (40/60)), and 60/40 (c/a (60/40)), and indicate that the ACN was incorporated at ratios greater than that in the reaction mixtures likely due to more rapid reaction of G5-PPI-NH$_2$ with ACN versus PO.

The NO release from the G5-PPI-PO/ACN conjugates at PO/ACN molar ratios of 27/73, 40/60, and 60/40, respectively, were intermediate to those synthesized based upon G5-PPI-NH$_2$ reactions with either PO (e.g., c-64) or ACN (e.g., a-64) alone. Furthermore, the NO release profiles were influenced by the molar ratio of PO/ACN composition. For instance, the NO release was prolonged for the PPI conjugates modified with lower molar ratio of PO/ACN. (2.90, 1.57, 1.10 h for 27/73, 40/60 and 60/40, respectively) (FIGS. 5A and 5B).

Simulated NO release profiles (expressed as percentages of total NO release, $y_{a:b}$) were determined by averaging the NO release profiles for G5-PPI-PO (a-64) ($y_{PO}$) and G5-PPI-ACN (a-64) ($y_{ACN}$) weighted with respect to the actual compositions of PO and ACN in these three PPI conjugates (expressed as molar ratios, a:b) (Eq. 1).

$$y_{a:b} = y_{PO} \times \frac{a}{a+b} + y_{ACN} \times \frac{b}{a+b} \quad (1)$$

Figure 5A:
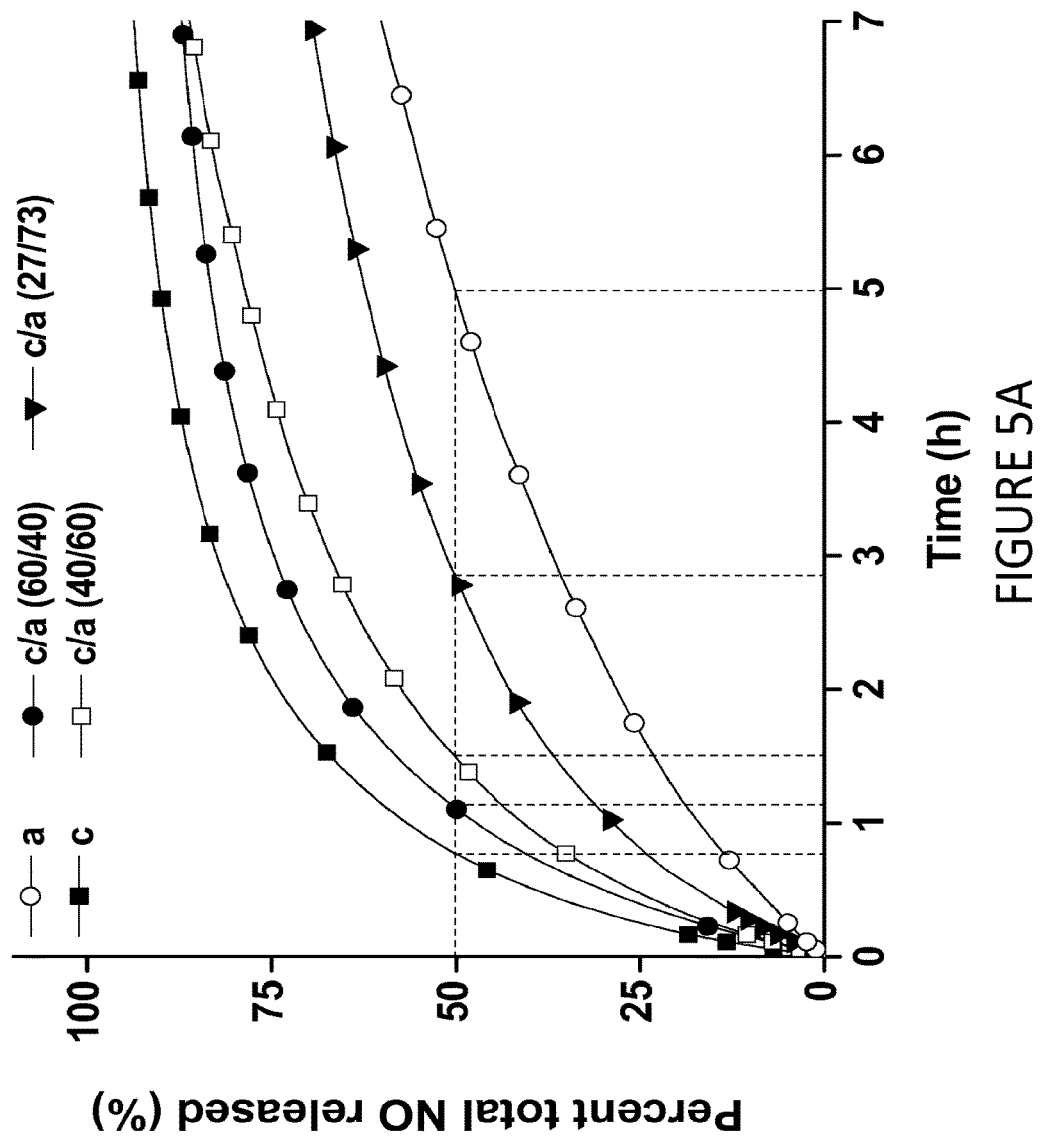
FIGS. 5A and 5B are graphs that provide (5A) an experimental plot of percent total NO released in PBS (pH=7.4) at 37° C. as a function of time for G5-PPI-PO, G5-PPI-ACN and G5-PPI-PO/ACN conjugates; (5B) a simulated plot of percent total NO released for G5-PPI-PO/ACN conjugates.
Figure 5B:
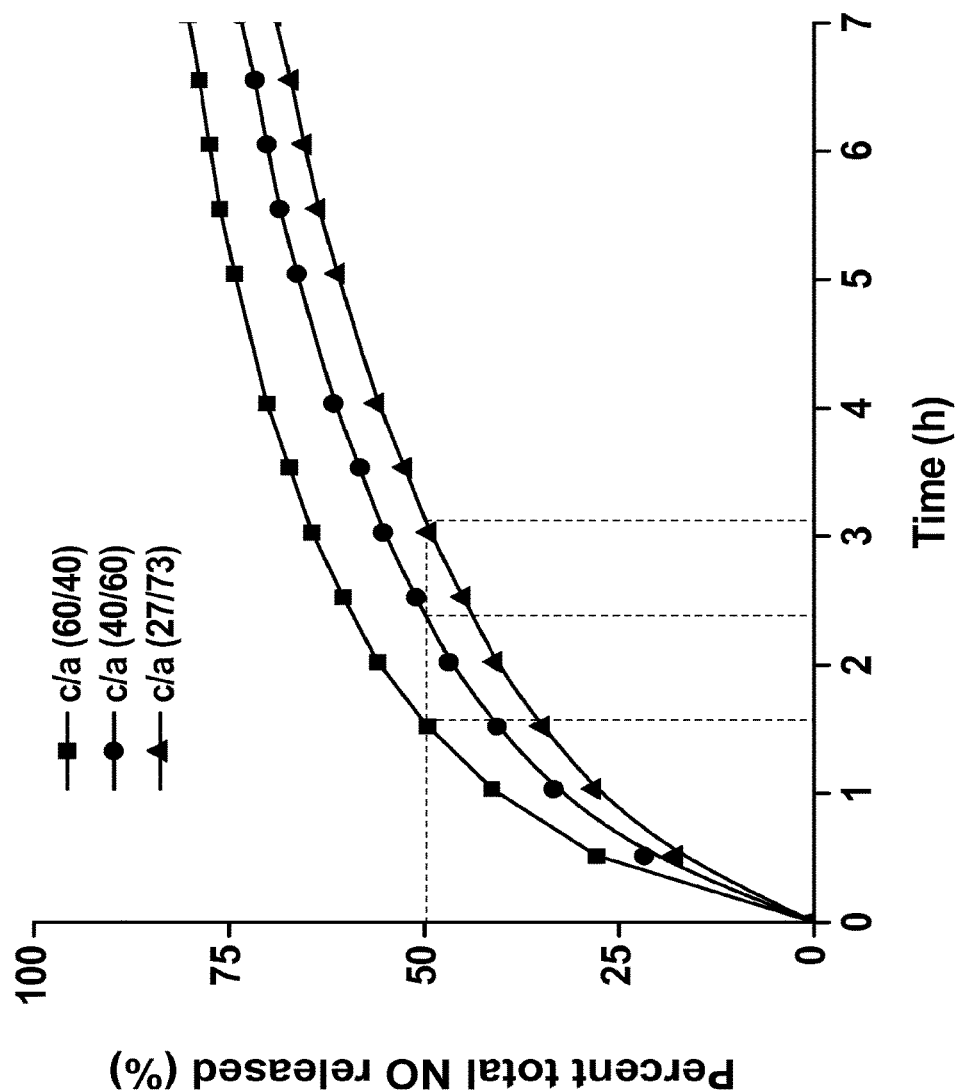

As shown in FIGS. 5A and 5B, the hybrid PPI conjugates were characterized by more rapid NO release than expected by the simulated data (NO release half-lives of 3.13, 2.42, 1.65 for c/a (27/73), c/a (40/60) and c/a (60/40), respectively). These results demonstrate that functionalization of PPI-NH$_2$ with a defined mixture of PO and ACN allows for further NO release tunability with access to NO release kinetics that are intermediate to those formed upon reactions with either PO or ACN exclusively.

The synthesis of diverse NO-releasing PPI dendrimers was achieved by chemical modification of exterior primary amines with ACN and PEG via conjugation addition or PO, ED, SO via ring opening reactions. The NO release from these dendrimers demonstrated that size (i.e., generation number or molecular weight) and exterior structures (e.g., steric environment, hydrophobicity, etc.) play important roles in NO release kinetics. Furthermore, the use of select NO donors with unique NO release kinetics and overall payloads may be exploited by utilizing these synthetic modification to create "multi-donor" dendrimers. The structurally diverse dendritic scaffolds extend the range and scope of secondary amine functionalities that may be designed into PPI conjugates.

Co-condensed Silica Examples

Example 6

Figure 6:
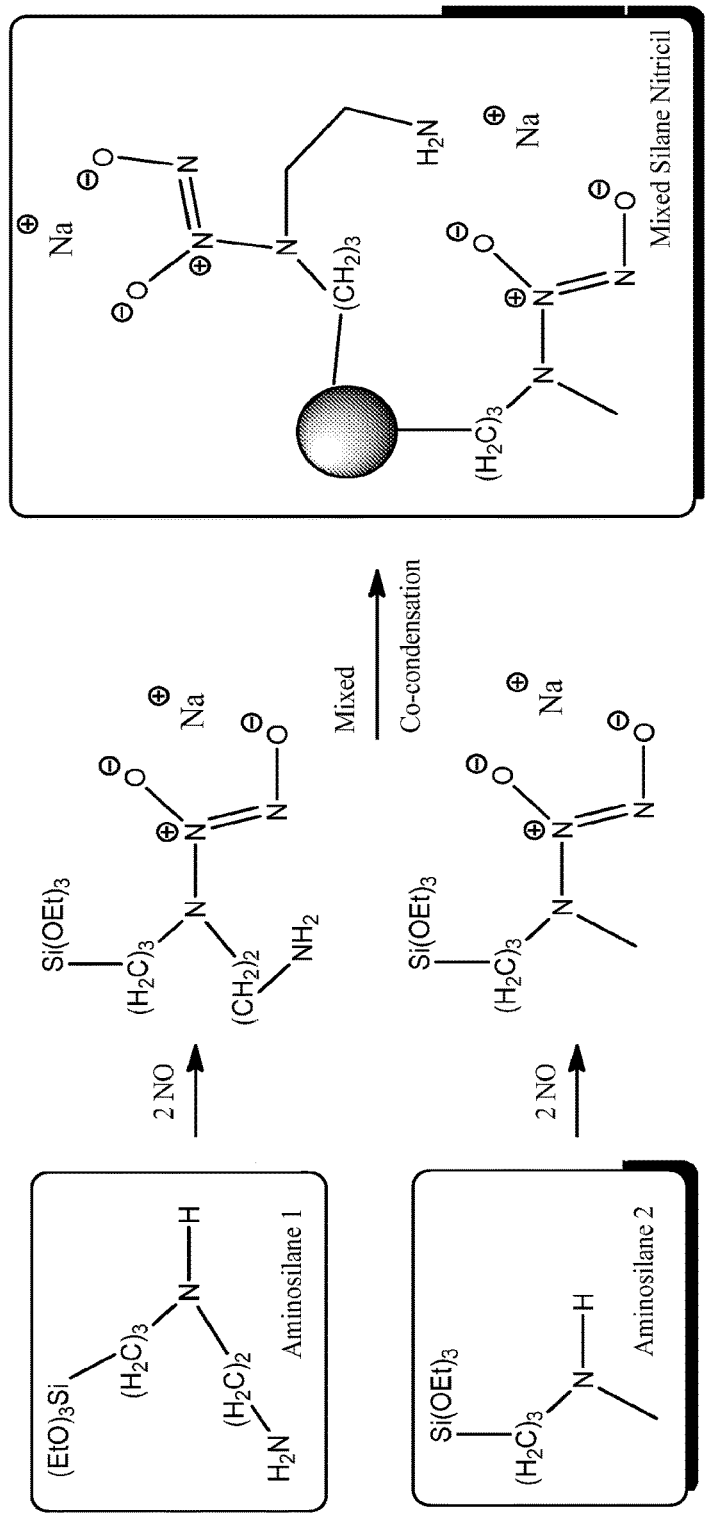
FIG. 6 is a schematic illustrating a synthesis of a multi-donor co-condensed silica network according to one embodiment of the invention.

An example of a synthesis of multi-donor co-condensed silica will now be provided and is shown schematically in FIG. 6. MAP3 diazeniumdiolate was mixed with AEAP diazeniumdiolate. The former molecule is known for its quick NO release and is able to rapidly establish and expose bacteria to a high concentration of nitric oxide, but the release lasts only a few minutes. On the other hand, AEAP diazeniumdiolate has a rather slow release profile with a half life in PH=7.4 buffer at over 3.5 hours. The constant exposure of bacteria to NO can effectively inhibit growth, however, it does not offer a high initial nitric oxide concentration that may be toxic to existing bacteria. By combining the two silanes onto the same polymeric structure, a programmable release profile can be achieved for improved effect in, for example, an antimicrobial application.

Figure 7:
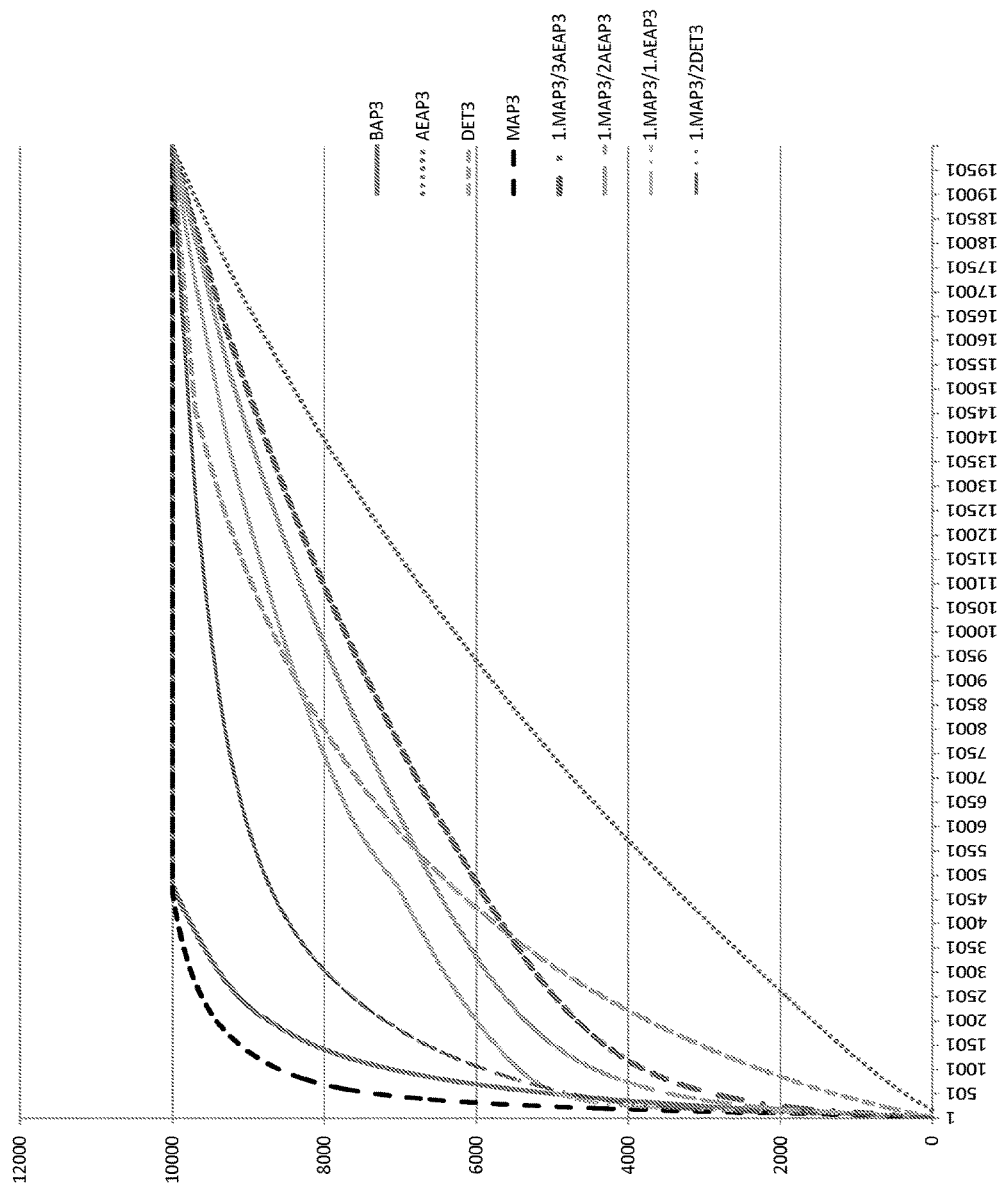
FIG. 7 is a graph of controlled release for single donor co-condensed silica and for various multi-donor combinations, with normalized total NO released.
Figure 8A:
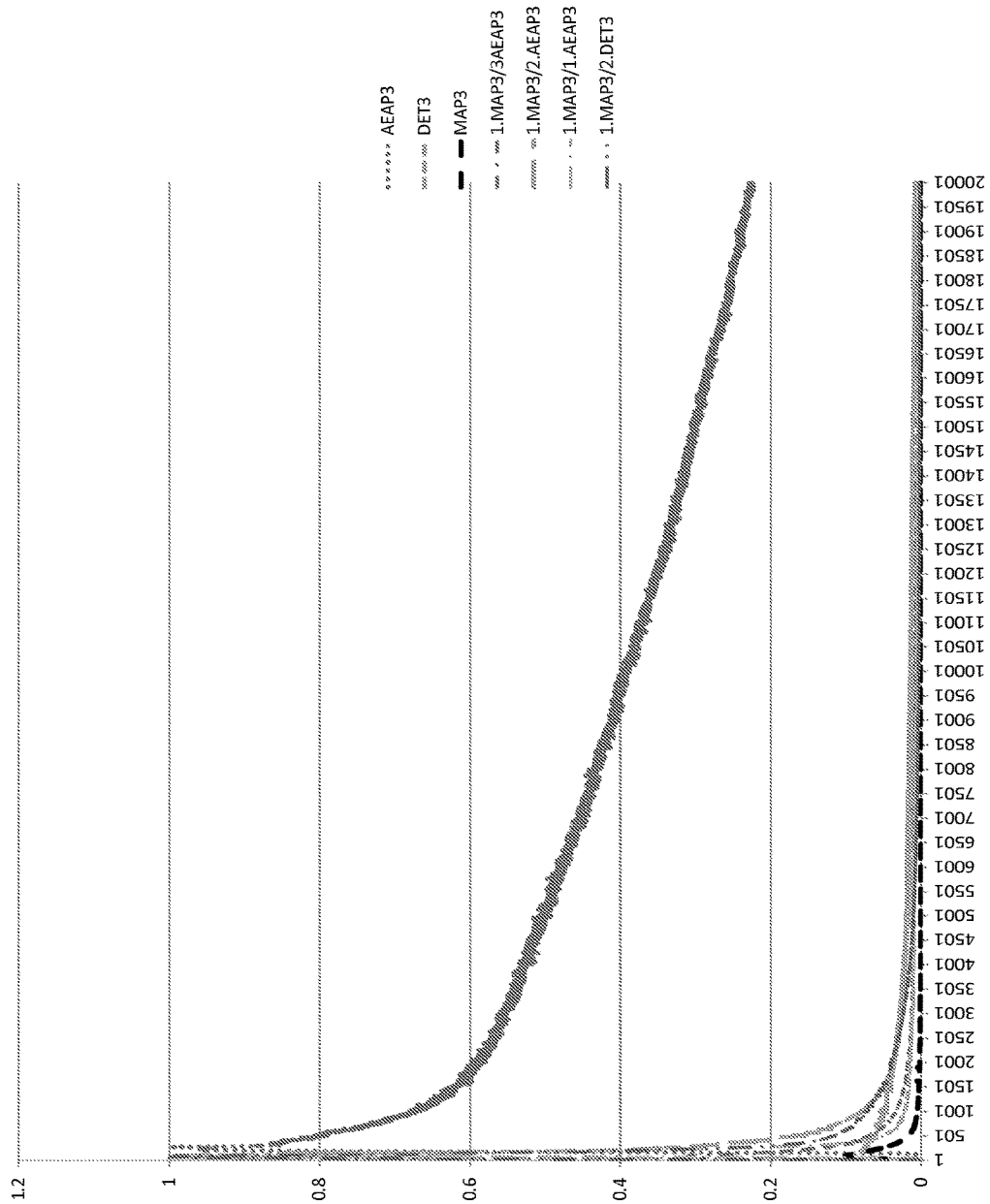
FIG. 8A is a graph of controlled release for single donor co-condensed silica and for various multi-donor combinations, with normalized max NO concentration.
Figure 8B:
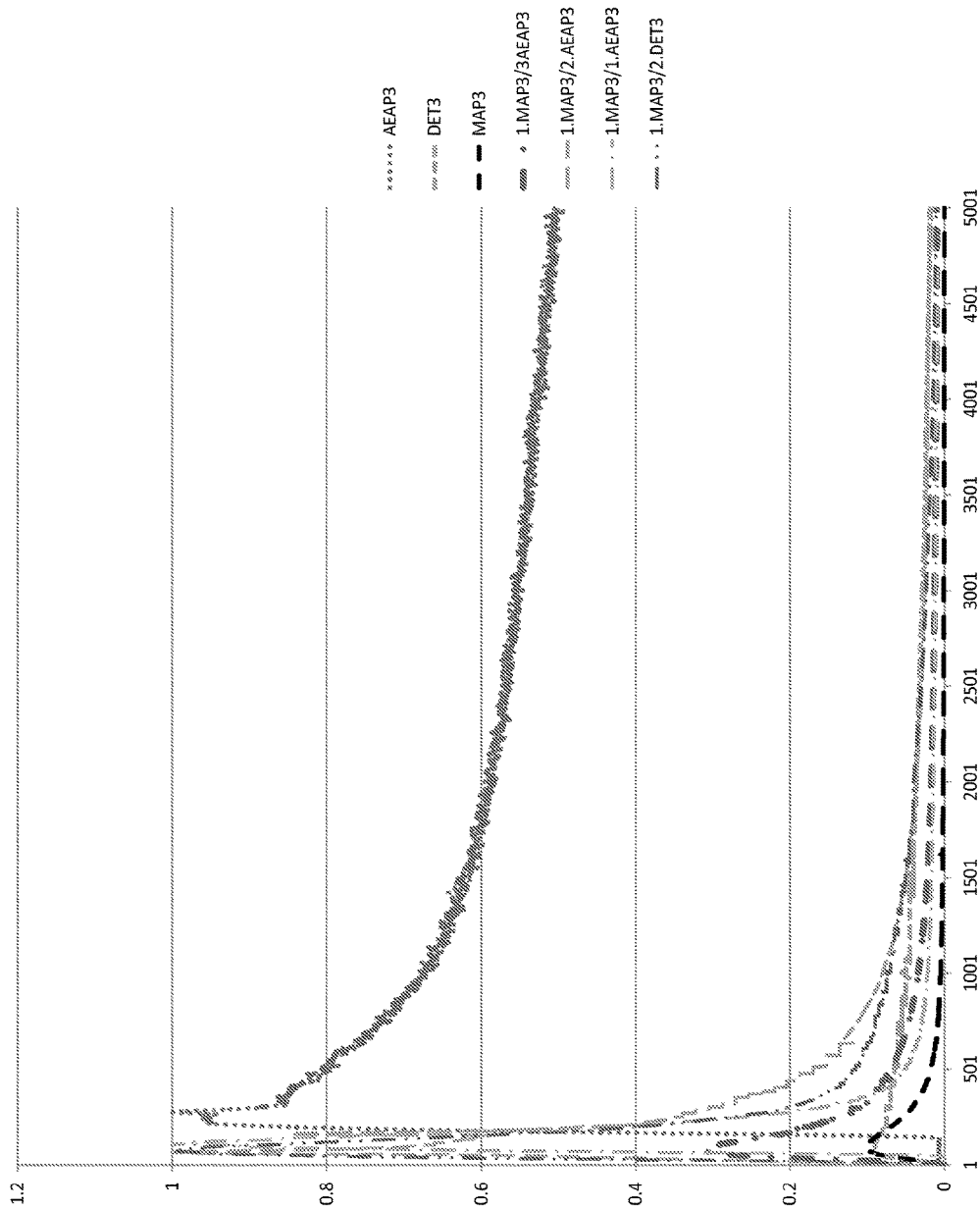
FIG. 8B is a graph of controlled release for single donor co-condensed silica and for various multi-donor combinations, with normalized max NO concentration.

A variety of single and multi-donor co-condensed silica macromolecules were synthesized. FIG. 7 shows the total NO released over a certain time period from different NO-releasing co-condensed silica macromolecules, with normalized total loading. FIGS. 8A and 8B illustrate the same release profiles with normalized maximum NO concentration. FIG. 8B illustrates the same release profiles, with normalized maximum NO concentration, as FIG. 8A, but is an expanded view of the release profiles. All release profiles were collected with a Nitric Oxide Analyzer under physiological condition at pH=7.4 and 37° C.

Figure 9A:
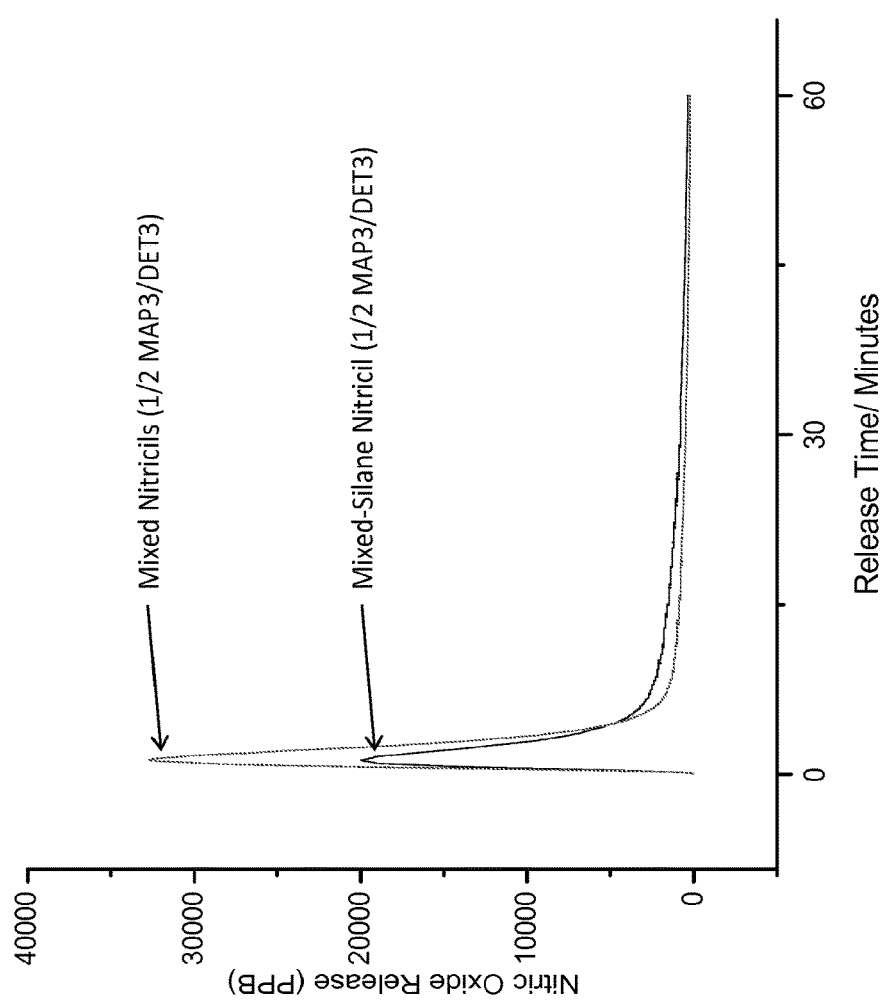
FIG. 9A is a graph that illustrates the difference in the release profile of a Multi-donor Nitricil™ and a Nitricil™ mixture.
Figure 9B:
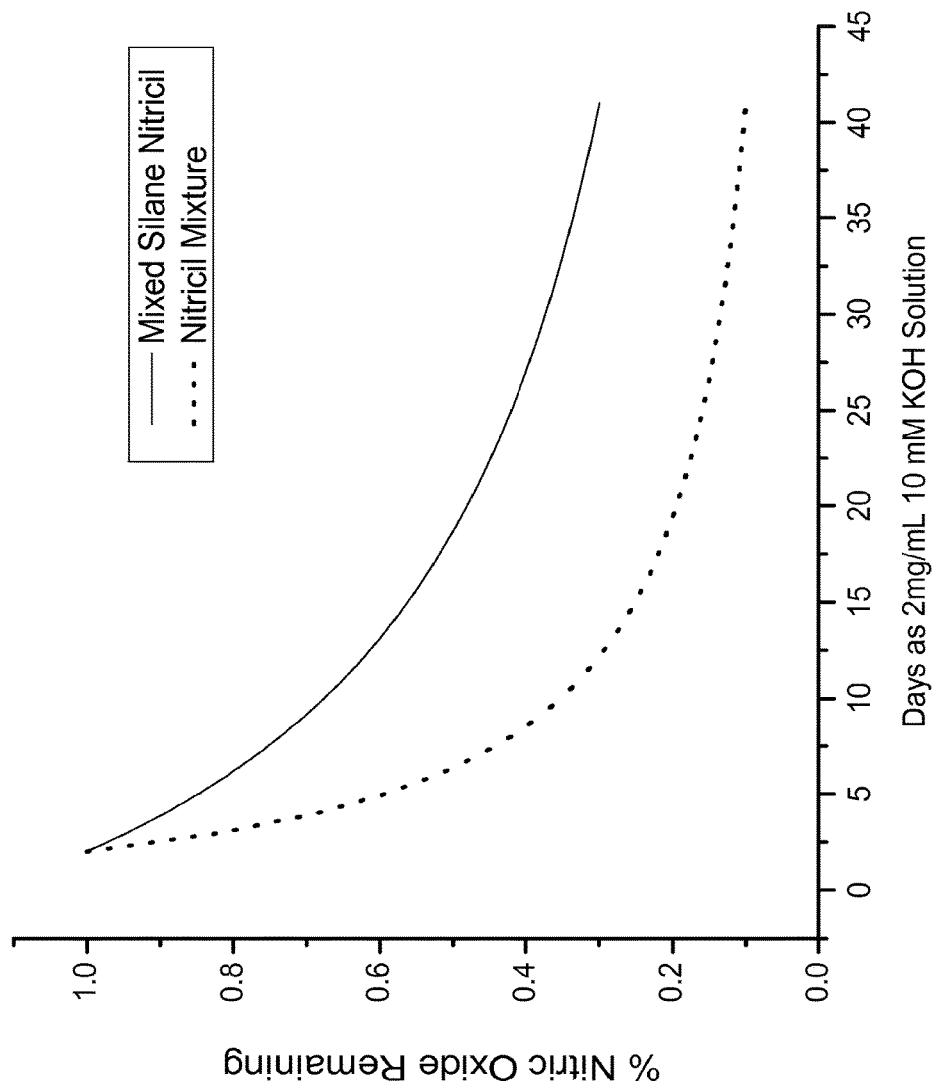
FIG. 9B is a graph that illustrations the difference in the degradation of a Multi-donor Nitricil™ and a Nitricil™ mixture in a pH 12 solution.
Figure 10:
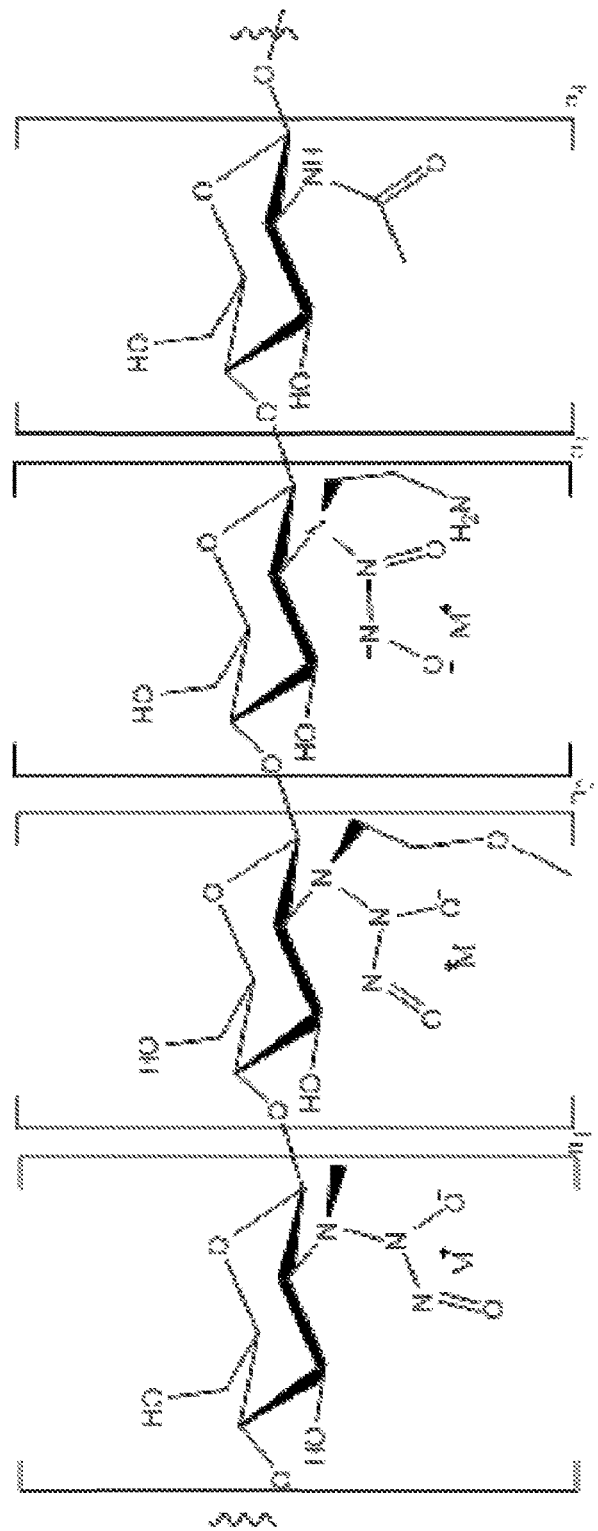
FIG. 10 is a schematic illustrating a multi-donor functionalized chitosan macromolecule with a portion of the scaffold remaining acetylated.

In addition, physical mixtures of separately synthesized single donor co-condensed silica macromolecules were also prepared. The idea of incorporating different NO-loaded aminosilanes onto one backbone has several advantages over a physical mixture of two different co-condensed silicas. One such advantage is homogeneity, and another is enhanced stability. FIGS. 9A and 9B illustrate the releasing curve of the multi-donor silica macromolecules and a physical mixture of the same donors on separate co-condensed silica scaffolds. It is clear that in the first hour shown the kinetics are different.

The co-condensed siloxane network with diazeniumdiolates incorporated throughout the macromolecule also has increased stability compared to each individual particles prepared with only one NO-loaded. FIG. 9B shows the degradation of the multi-donor silica slowed down significantly compare to the physical mixtures. This discovery may be extremely useful in increasing the ability to preserve the NO until triggered release at the location of targeted medical application. While not wishing to be bound to any particular theory, the mechanism for the stability increase appears to be a coordinated effort of both steric hindrance of the proton attack and intramolecular hydrogen bonding between different silanes. The intramolecular protective interaction is not available in the mixed solid, which resulted in a faster degradation.

To make aminosilane diazeniumdiolate monomers, the aminosilane is added into a high pressure reaction vessel together with 1 equivalent of NaOMe (25-30% w.w) MeOH solution. An equal volume of dried methanol is also added. The reactor is pump/purged with argon at 100 psi for three times before NO was pumped into the reactor. The initial reaction pressure is at least 300 psi and as high as 420 psi. The pressure is kept at this range with refill. The reaction is stopped at two hours and the content is used in the following condensation reactions without further isolation.

To make NO-releasing co-condensed silica with programmed release profile, the different silane diazeniumdiolate monomer solutions were mixed at the pre-set ratios. The mixture is then added into a flask with pre-cooled ethanol with nitrogen protection. The mixture is further cooled to −15° C. and pre-set amount of backbone silane (TEOS or TMOS) is added. When the mixture temperature equilibriums to −15° C., the ammonium hydroxide aqueous solution is added. The reaction is then warmed rapidly to 15° and stirred for additional 3 hours. The content is then filtered. The solid is washed with dry ethanol twice and then dried extensively.

TABLE 2

An Example of Programmable Release from Two Silanes

| Sample | Composition | Ratio | Half Life/ minutes | Total NO umol/mg | Reference |
|---|---|---|---|---|---|
| 1 | MAP3/AEAP3 | 100/0 | 4 | 4.5 | 10-7-132 |
| 2 | MAP3/AEAP3 | 50/50 | 23 | 4.1 | 11-4-61 |
| 3 | MAP3/AEAP3 | 33/66 | 70 | 3 | 11-4-59 |
| 4 | MAP3/AEAP3 | 25/75 | 112 | 2.7 | 11-4-60 |
| 5 | MAP3/AEAP3 | 0/100 | 210 | 5.1 | 11-4-29 |

It is clear that the diazeniumdiolate degradation is the same mechanism as the NO release path through proton initiated reaction illustrated below. Therefore, water/moisture are among the top reasons for degradation. Experimental data have shown that some diazeniumdiolate-functionalized co-condensed silica are hygroscopic, and the intrinsic water may be tightly bounded to the silicate in the back bone of the polymer. The hygroscopic property of the diazeniumdiolate-functionalized co-condensed silica may lead to degradation of the diazeniumdiolate.

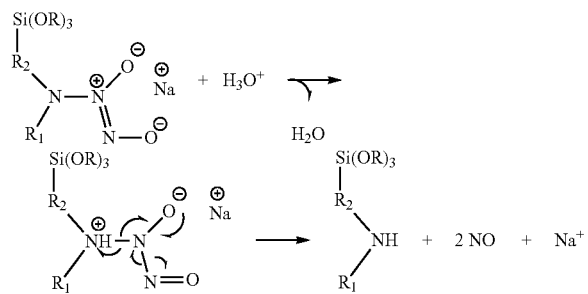

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A nitric oxide (NO)-releasing co-condensed silica macromolecule comprising:
   a co-condensed silica network comprising N-diazeniumdiolate functionalized N-ethylaminoisobutyltrimethoxysilane (EAiB3), N-diazeniumdiolate functionalized [3-(methylamino)propyl]trimethoxysilane (MAP3), and tetraethyl orthosilicate (TEOS).

2. The NO-releasing co-condensed silica macromolecule of claim 1, wherein EAiB3 and MAP3 are present in a ratio from about 1:1 to about 3:1 (EAiB3:MAP3).

3. The NO-releasing co-condensed silica macromolecule of claim 1, wherein EAiB3 and MAP3 are present in a ratio of about 1:1 (EaiB3:MAP3).

4. The NO-releasing co-condensed silica macromolecule of claim 1, wherein EaiB3 and MAP3 are present in a ratio of about 2:1 (EaiB3:MAP3).

5. The NO-releasing co-condensed silica macromolecule of claim 1, wherein EaiB3 and MAP3 are present in a ratio of about 3:1 (EaiB3:MAP3).

6. The NO-releasing co-condensed silica macromolecule of claim 1, wherein EaiB3 and/or MAP3 comprise a $Na^+$, $K^+$, $Cs^+$, $Li^+$, $NH_4^+$, or other quaternary ammonium cation.

7. The NO-releasing co-condensed silica macromolecule of claim 1, wherein EaiB3 and/or MAP3 comprise a sodium cation.

8. The NO-releasing co-condensed silica macromolecule of claim 1, wherein EaiB3 and/or MAP3 comprise a potassium cation.

9. The NO-releasing co-condensed silica macromolecule of claim 1, wherein EaiB3 and/or MAP3 comprise a lithium cation.

10. The NO-releasing co-condensed silica macromolecule of claim 1, wherein TEOS is anionic.

11. A nitric oxide (NO)-releasing co-condensed silica macromolecule comprising:
    a co-condensed silica network comprising N-diazeniumdiolate functionalized aminoethylaminopropyl trimethoxysilane (AEAP3), N-diazeniumdiolate functionalized [3-(methylamino)propyl]trimethoxysilane (MAP3), and tetra methyl orthosilicate (TEOS).

12. The NO-releasing co-condensed silica macromolecule of claim 1, wherein AEAP3 and MAP3 are present in a ratio from about 1:1 to about 3:1 (AEAP3:MAP3).

13. The NO-releasing co-condensed silica macromolecule of claim 1, wherein AEAP3 and MAP3 are present in a ratio of about 1:1 (AEAP3:MAP3).

14. The NO-releasing co-condensed silica macromolecule of claim 1, wherein AEAP3 and MAP3 are present in a ratio of about 2:1 (AEAP3:MAP3).

15. The NO-releasing co-condensed silica macromolecule of claim 1, wherein AEAP3 and MAP3 are present in a ratio of about 3:1 (AEAP3:MAP3).

16. The NO-releasing co-condensed silica macromolecule of claim 1, wherein AEAP3 and/or MAP3 comprise a $Na^+$, $K^+$, $Cs^+$, $Li^+$, $NH_4^+$, or other quaternary ammonium cation.

17. The NO-releasing co-condensed silica macromolecule of claim 1, wherein AEAP3 and/or MAP3 comprise a sodium cation.

18. The NO-releasing co-condensed silica macromolecule of claim 1, wherein AEAP3 and/or MAP3 comprise a potassium cation.

19. The NO-releasing co-condensed silica macromolecule of claim 1, wherein AEAP3 and/or MAP3 comprise a lithium cation.

20. A nitric oxide (NO)-releasing co-condensed silica macromolecule comprising:
  a co-condensed silica network comprising N-diazeniumdiolate functionalized aminoethylaminopropyl trimethoxysilane (AEAP3), N-diazeniumdiolate functionalized [3-(methylamino)propyl]trimethoxysilane (MAP3), and tetraethyl orthosilicate (TMOS).

\* \* \* \* \*

UNITED STATES PATENT AND TRADEMARK OFFICE
CERTIFICATE OF CORRECTION

PATENT NO. : 10,435,357 B2
APPLICATION NO. : 16/239069
DATED : October 8, 2019
INVENTOR(S) : Schoenfisch et al.

It is certified that error appears in the above-identified patent and that said Letters Patent is hereby corrected as shown below:

In the Specification

Column 4, Line 14: Please correct "$C_{is}$" to read -- $C_{1-5}$ --

Column 11, Line 32: Please correct "10" to read -- 10 μm --

Column 16, Line 49: Please correct "G5-PPI-NI-1$_2$" to read -- G5-PPI-NH$_2$ --

Column 16, Line 59: Please correct "3.40-330" to read -- 3.40-3.70 --

Column 19, Line 41: Please correct "~4.7-3.6" to read -- ~1.7-3.6 --

Column 21, Line 54: Please correct "(ypo)" to read -- (y$_{PO}$) --

Signed and Sealed this
Fourth Day of February, 2020

Andrei Iancu
*Director of the United States Patent and Trademark Office*